US012217442B2

(12) United States Patent
Datteri et al.

(10) Patent No.: US 12,217,442 B2
(45) Date of Patent: Feb. 4, 2025

(54) SYSTEMS AND METHODS FOR REGISTRATION BETWEEN PATIENT SPACE AND IMAGE SPACE USING REGISTRATION FRAME APERTURES

(71) Applicant: Medtronic Navigation, Inc., Louisville, CO (US)

(72) Inventors: Ryan D. Datteri, Denver, CO (US); Ganesh Saiprasad, Broomfield, CO (US); Steven Hartmann, Superior, CO (US); Matthew F. Dicorleto, Boulder, CO (US); Brandon Merkl, Arvada, CO (US)

(73) Assignee: Medtronic Navigation, Inc., Lafayette, CO (US)

( * ) Notice: Subject to any disclaimer, the term of this patent is extended or adjusted under 35 U.S.C. 154(b) by 412 days.

(21) Appl. No.: 17/650,053

(22) Filed: Feb. 4, 2022

(65) Prior Publication Data

US 2022/0254040 A1 Aug. 11, 2022

Related U.S. Application Data

(60) Provisional application No. 63/147,897, filed on Feb. 10, 2021.

(51) Int. Cl.
*G06T 7/00* (2017.01)
*A61B 6/03* (2006.01)
(Continued)

(52) U.S. Cl.
CPC .............. *G06T 7/337* (2017.01); *A61B 6/032* (2013.01); *A61B 34/20* (2016.02); *G06T 3/14* (2024.01);
(Continued)

(58) Field of Classification Search
CPC ......... G06T 7/337; G06T 3/14; G06T 7/0014; G06T 7/174; G06T 7/248; G06T 7/68;
(Continued)

(56) References Cited

U.S. PATENT DOCUMENTS

2012/0201421 A1* 8/2012 Hartmann ............ A61B 6/5235
382/103
2018/0144472 A1* 5/2018 Kullberg ............ G01R 33/4828

FOREIGN PATENT DOCUMENTS

EP 1510182 A2 * 3/2005 ............. A61B 34/20
EP 2676627 A2 12/2013

OTHER PUBLICATIONS

International Search Report for related Application No. PCT/US2022/015943; Mailing Date: Jun. 2, 2022; 3 pages.
(Continued)

*Primary Examiner* — Ping Y Hsieh
(74) *Attorney, Agent, or Firm* — Harness, Dickey & Pierce, P.L.C.

(57) ABSTRACT

Systems and methods for performing registration between a patient space and an image space are disclosed herein. Systems using such methods may identify a pose of a registration frame having one or more apertures within the patient space using a tracking system. Image data corresponding to the image space having an image of the registration frame is taken. A plurality of aperture locations within the image data (corresponding to the apertures of the registration frame) are identified in the image data. Aperture representations from a model of the registration frame are matched to these aperture locations to determine a pose of the registration frame within the image space. A transform between the patient space and the image space is generated based on the pose of the registration frame within the patient space and the pose of the registration frame within the image
(Continued)

space. Optimization methods for this transform are discussed.

19 Claims, 14 Drawing Sheets

(51) Int. Cl.
    *A61B 34/20*     (2016.01)
    *G06T 3/14*     (2024.01)
    *G06T 7/174*     (2017.01)
    *G06T 7/246*     (2017.01)
    *G06T 7/33*     (2017.01)
    *G06T 7/68*     (2017.01)
    *G06T 7/73*     (2017.01)
(52) U.S. Cl.
    CPC ............ *G06T 7/0014* (2013.01); *G06T 7/174* (2017.01); *G06T 7/248* (2017.01); *G06T 7/68* (2017.01); *G06T 7/74* (2017.01); *A61B 2034/2065* (2016.02); *G06T 2207/10081* (2013.01); *G06T 2207/20132* (2013.01); *G06T 2207/20224* (2013.01); *G06T 2207/30004* (2013.01); *G06T 2207/30204* (2013.01)

(58) Field of Classification Search
    CPC ............. G06T 7/74; G06T 2207/10081; G06T 2207/20132; G06T 2207/20224; G06T 2207/30004; G06T 2207/30204; G06T 2207/10072; G06T 2207/20036; G06T 2207/30012; G06T 2207/30016; G06T 2207/30052; G06T 7/73; A61B 6/032; A61B 34/20; A61B 2034/2065; A61B 2017/00725; A61B 2034/2055; A61B 2090/3762; A61B 2090/3937; A61B 2090/3983; A61B 2090/3991; A61B 2090/502; A61B 6/12
    See application file for complete search history.

(56) References Cited

OTHER PUBLICATIONS

Written Opinion for related Application No. PCT/US2022/015943; Mailing Date: Jun. 2, 2022; 7 pages.

* cited by examiner

SYSTEMS AND METHODS FOR REGISTRATION BETWEEN PATIENT SPACE AND IMAGE SPACE USING REGISTRATION FRAME APERTURES

RELATED APPLICATIONS

This application claims priority to U.S. Provisional Application No. 63/147,897 filed on Feb. 10, 2021 and titled "SYSTEMS AND METHODS FOR REGISTRATION BETWEEN PATIENT SPACE AND IMAGE SPACE USING REGISTRATION FRAME APERTURES" which is hereby incorporated by reference in its entirety.

TECHNICAL FIELD

The present disclosure relates generally to surgical procedures and particularly to registration of image space to patient space such that instruments (or other objects) posed in patient space during surgical procedures may be appropriately represented in a corresponding pose in image space.

DETAILED DESCRIPTION

Figure 1:
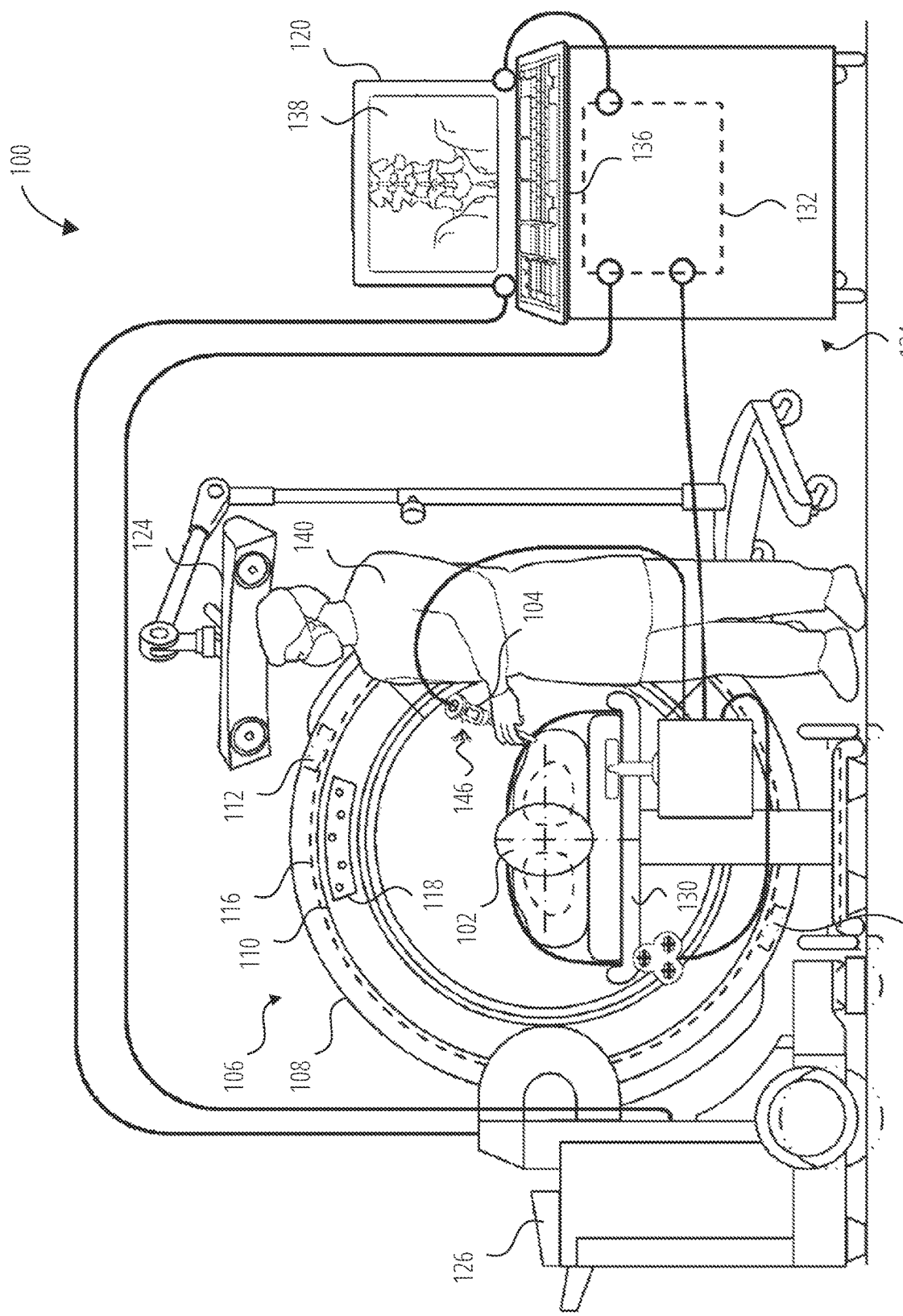
FIG. 1 is a diagrammatic view illustrating an overview of a navigation system that can be used for various procedures, according to various embodiments.

An instrument (or other object) may be navigated relative to a patient while performing a surgical procedure on the patient. The instrument may be tracked within the space defined by the patient (the "patient space").

The patient may have been imaged previously to or during the surgical procedure to obtain a pre-operative scan. This image data may exist within an "image space" and may correspond to the patient space. This image data corresponding to the images space may be displayed/displayable on, for example, a monitor or other display device.

It may be desirable to reproduce a representation of the instrument (or other object such as a tracker attached to vertebrae) that is being tracked in patient space in the image space as well. For example, in cases where the image data of the patient in image space shows the inside of the patient, it may be valuable to see where the instrument is located within the patient after (part of) the instrument has been inserted into the patient. In these cases, while the (part of the) instrument cannot be seen in patient space, the representation of the instrument in the image space may be observed on the display device.

To facilitate this, a transform may be determined that maps between patient space and image space. Then, applying the pose (e.g., position and/or orientation) of the instrument as tracked in patient space and the transform, the corresponding pose of the instrument in image space may be determined, and an appropriate representation of the instrument corresponding to this image space pose may be provided within the image data.

Embodiments may be understood by reference to the drawings, wherein like parts are designated by like numerals throughout. It will be readily understood by one of ordinary skill in the art having the benefit of this disclosure that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

It will be appreciated that various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

FIG. 1 is a diagrammatic view illustrating an overview of a navigation system 100 that can be used for various procedures. The navigation system 100 can be used to track the location of an implant, such as a spinal implant or orthopedic implant, relative to a patient 102. Also, the navigation system 100 can track the pose of an instrument 104, such as a biopsy needle or resection instrument. It should further be noted that the navigation system 100 may be used to navigate any type of instrument, implant, or delivery system, including: guide wires, arthroscopic systems, orthopedic implants, spinal implants, deep brain stimulation (DBS) probes, etc. Moreover, the instruments may be used to navigate or map any region of the body. The navigation system 100 and the various instruments may be used in any appropriate procedure, such as one that is generally minimally invasive or an open procedure.

The navigation system 100 includes an imaging device 106 that is used to acquire pre-, intra-, or post-operative or real-time image data of a subject, such as a patient 102. It will be understood, however, that any appropriate subject can be imaged and any appropriate procedure may be performed relative to the subject. The imaging device 106 may have a generally annular gantry housing 108 and an image capturing portion 110. The image capturing portion 110 may include an emission portion 112 and an image receiving portion 114 located generally or as practically possible 180 degrees from each other and mounted on a rotor (not illustrated) relative to a rail 116. The image capturing portion 110 can be operable to rotate 360 degrees during image acquisition. The image capturing portion 110 may rotate around a central point or axis, allowing image data of the patient 102 to be acquired from multiple directions or in multiple planes. In one example, the imaging device 106 can utilize flat plate technology having a 1,720 by 1,024 pixel viewing area.

The position of the image capturing portion 110 can be precisely known relative to any other portion of the imaging device 106. The imaging device 106, according to various embodiments, can know and recall precise coordinates relative to a fixed or selected coordinate system. This can allow the imaging device 106 to know its position relative to the patient 102 or other references. In addition the precise knowledge of the position of the image capturing portion 110 can be used in conjunction with a tracking system to determine the position of the image capturing portion 110 and the image data relative to the tracked subject, such as the patient 102.

The imaging device 106 can also be tracked with a tracking device 118. The image data defining an image space acquired of the patient 102 can, according to various embodiments, be inherently or automatically registered relative to patient space. The patient space can be the space defined by a patient 102 in the navigation system 100. The automatic registration can be achieved by including the tracking device 118 on the imaging device 106 and/or the determinable precise location of the image capturing portion 110. According to various embodiments, as discussed herein, registration frame apertures and other features can also be used to allow for registration, automatic or otherwise (e.g., see FIG. 3). It will be understood that image data can be acquired of any subject that defines the patient space. Registration allows for a translation between patient space and image space.

The patient 102 can also be tracked or fixed within the navigation system 100 to allow for registration. As discussed further herein, registration of the image space to the patient space allows for navigation of an instrument 104 with the image data. When navigating the instrument 104, a position of the instrument 104 can be illustrated relative to image data acquired of the patient 102 on a display device 120. Various tracking systems, such as tracking systems including an optical localizer 124 can be used to track the instrument 104.

More than one type of tracking system can be used to track the instrument 104 in the navigation system 100. According to various embodiments, these tracking systems can include, for example, an optical tracking system having an optical localizer 124. These tracking systems can be used to track selected tracking devices, as discussed herein. It will be understood, unless discussed otherwise, that a tracking device can be a portion trackable with a selected tracking system. A tracking device need not refer to the entire member or structure to which the tracking device is affixed or associated.

It is appreciated that the imaging device 106 may be of many different possible imaging devices (which may or may not be shaped as illustrated in FIG. 1). In some examples, the imaging device 106 is a computed tomography (CT) device.

An imaging device controller 126 that may control the imaging device 106 can receive the image data generated at the image capturing portion 110 and store the images for later use. The imaging device controller 126 can also control the rotation of the image capturing portion 110 of the imaging device 106. It will be understood that the imaging device controller 126 may in some embodiments be hosted on a system that is not physically integrated into the imaging device 106 (e.g., on a portable computing system that is physically and/or logically connected to the imaging device 106).

The patient 102 can be fixed onto an operating table 130. Patient positioning devices can be used with the operating table 130.

The position of the patient 102 relative to the imaging device 106 can be determined by the navigation system 100. The tracking device 118 can be used to track and locate at least a portion of the imaging device 106, for example the gantry housing 108. The patient 102 can be tracked with a tracking device, such as one used as a dynamic registration frame, as discussed further herein. Accordingly, the position of the patient 102 relative to the imaging device 106 can be determined. Further, the location of the image capturing portion 110 can be determined relative to the gantry housing 108 due to its precise position on the rail 116 within the gantry housing 108, substantially inflexible rotor, etc. In some examples, the imaging device 106 may be accurate within 10 microns.

In operation, the imaging device 106 can generate and/or emit radio waves from the emission portion 112 that propagate through the patient 102 and are received by the receiving portion 114. The image capturing portion 110 generates image data representing the intensities of the received radio waves. Typically, the image capturing portion 110 can include an image intensifier that first converts the radio waves to visible light and a camera (e.g., a charge couple device) that converts the visible light into digital image data. The image capturing portion 110 may also be a digital device that converts radio waves directly to digital image data for forming images, thus potentially avoiding distortion introduced by first converting to visible light.

Two dimensional and/or three dimensional image data that may be taken by the imaging device 106 can be captured and stored in the imaging device controller 126. Multiple image data taken by the imaging device 106 may also be captured and assembled to provide a larger view or image of a whole region of a patient 102, as opposed to being directed to only a portion of a region of the patient 102. For example, multiple image data of the spine of the patient 102 may be appended together to provide a full view or complete set of image data of the spine.

The image data can then be forwarded from the imaging device controller 126 to a navigation computer and/or processor system 132 that can be a part of a controller or workstation 134 having the display device 120 and a user interface 136. It will also be understood that the image data is not necessarily first retained in the imaging device controller 126, but may also be directly transmitted to the workstation 134. The workstation 134 can provide facilities for displaying the image data as an image 138 on the display device 120, saving, digitally manipulating, or printing a hard copy image of the received image data. The user interface 136, which may be a keyboard, mouse, touch pen, touch screen, or other suitable device, allows a user 140 to provide inputs to control the imaging device 106, via the imaging device controller 126, or adjust the display settings of the display device 120. The workstation 134 may also direct the imaging device controller 126 to adjust the image capturing portion 110 of the imaging device 106 to obtain various two dimensional images along different planes in order to generate representative two dimensional and three dimensional image data.

The navigation system 100 can further include a tracking system. In some cases, this tracking system may be an optical tracking system. The optical tracking system may include a localizer, such as the optical localizer 124 (which may be, e.g., one or more infrared cameras and one or more infrared sources). The optical tracking system may include an optical tracking device 146 associated with the instrument 104. Light from the infrared sources of the optical localizer 124 may be reflected off optical tracking device 146 and back to a camera of the optical localizer 124. In this way, the optical tracking system can track the optical tracking device 146 (and thus the instrument 104).

It will be understood that the navigation system 100 may also be or include any appropriate tracking system, including an acoustic tracking system, a radiation tracking system, a radar tracking system, a lidar tracking system, etc.

Wired or physical connections can interconnect the portions of the navigation system 100, such as the tracking systems being used, the imaging device 106, etc. Alternatively, various portions, such as the instrument 104, may employ a wireless communications channel as opposed to being coupled directly to any other portion of the navigation system 100.

Various portions of the navigation system 100 (such as the instrument 104) can be equipped with at least one, and sometimes multiple, of the tracking devices 118. The instrument can also include more than one type or modality of tracking device. The instrument 104 can include a graspable or manipulatable portion at a proximal end, and an optical tracking device 146 may be fixed near the manipulatable portion of the instrument 104.

According to various embodiments, the navigation system 100 can be used to track the instrument 104 relative to the patient 102. The instrument 104 can be tracked with the tracking system, as discussed above. Image data of the patient 102, or an appropriate subject, can be used to assist the user 140 in guiding the instrument 104. The image data, however, is registered to the patient 102. The image data defines an image space that is registered to the patient space defined by the patient 102. The registration can be performed as discussed herein, automatically, manually, or in combinations thereof.

A registration process generates a transform that is used to map a pose of the instrument 104 (or another tracked item) within the patient space (as determined by one or more tracking systems, such as an optical tracking system using the optical localizer 124, in the manner described above) to a corresponding pose in the image data corresponding to the image space. The transform is used on the tracked pose of the instrument 104 (or other tracked item) in patient space in order determine a pose at which to place a representation of the instrument within the image space. The representation of the instrument is then displayed on, for example, the display device 120 at the proper location within the image 138.

Figure 2A:
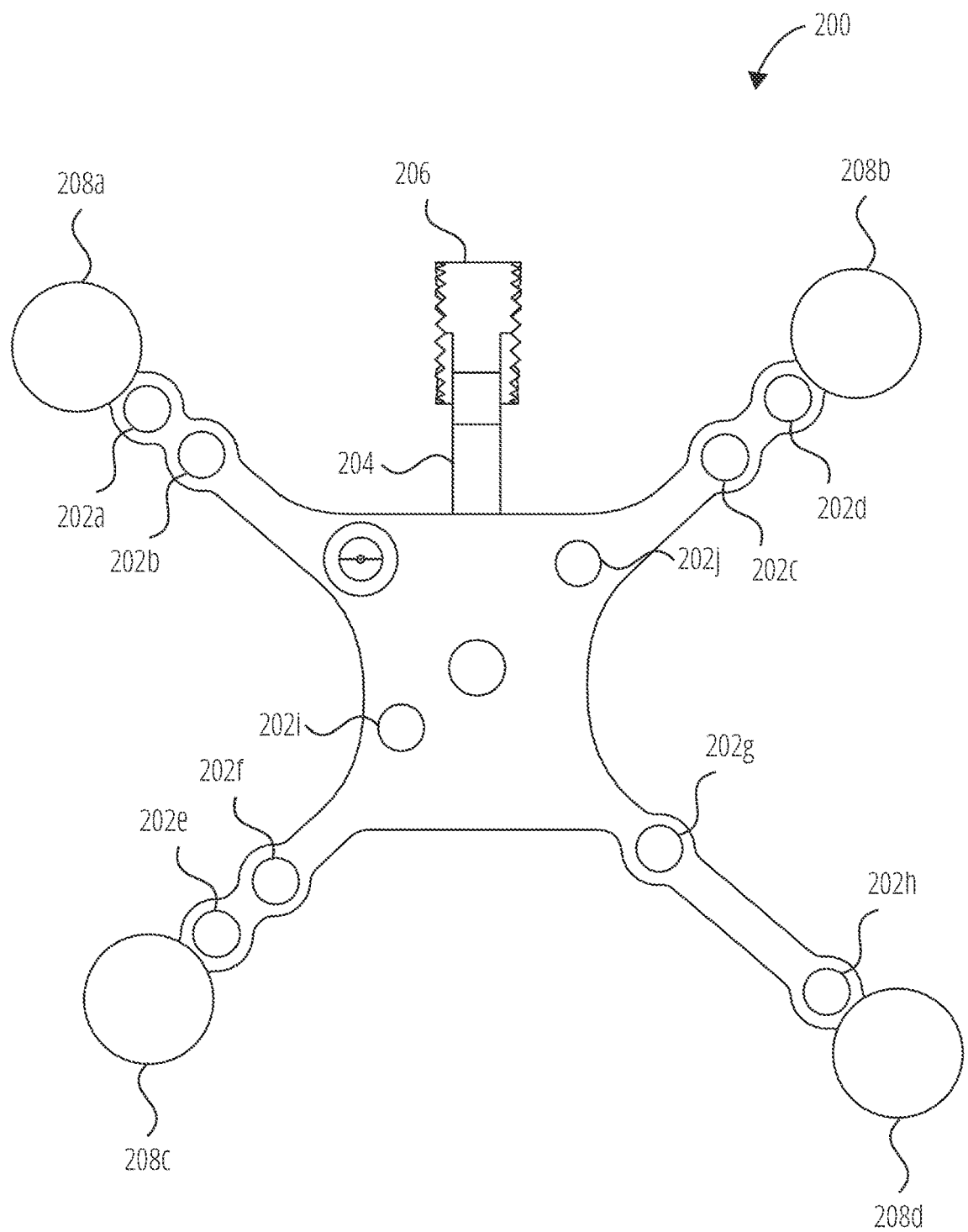
FIG. 2A illustrates a registration frame according to an embodiment.

FIG. 2A illustrates a registration frame 200 according to an embodiment. As will be described in further detail below, systems and methods disclosed herein use the registration frame 200 (and/or other analogous frames) to perform a registration process that, among other things, generates a transform that may be used to correspond a pose of the instrument 104 (or other tracked item) in patient space to a pose of the instrument 104 in image space, thereby enabling the method 1000 to provide a representation of the instrument 104 (or other tracked item) in the image space.

The material of the registration frame 200 may be or include materials that are capable of being imaged by an imaging device in a high quality manner (e.g., that will show within image data with a relatively high intensity). For example, for use with an imaging device that is a CT imaging device, the material of the registration frame 200 may be or include titanium.

The registration frame 200 may further include one or more apertures 202a-202j. While the apertures 202a-202j have been illustrated here as cylindrical (see also FIG. 2B), it is contemplated that other aperture shapes are possible for use with systems and methods herein. For example, in at least some embodiments herein, apertures in the shape of right prisms (square right prisms, dodecahedral right prisms, etc.) may be used. Further, at least some embodiments herein may allow for shapes that are not strictly prisms but that extend through the entire registration frame 200 in an orthogonal fashion (e.g., half cylinders).

The registration frame 200 may further include a shaft 204. The shaft 204 may extend from a surface of the registration frame 200 and end in a sunburst 206 useful for connecting the registration frame 200 to another device, in the manner described and/or illustrated elsewhere herein.

The registration frame 200 may further include one or more tracking devices for use with one or more tracking systems, in the manner described above. In the embodiment of FIG. 2A, such tracking devices include infrared (IR) reflectors 208a-208d. It is contemplated that other types of tracking devices may be used on the registration frame 200 in other embodiments. The placement of the IR reflectors 208a-208d is given by way of example and not by way of limitation.

It is further contemplated that in some embodiments, the registration frame 200 may not include tracking devices at all. For example, the registration process may use the shape of the registration frame 200 rather than tracking devices.

A pose (i.e., a position and an orientation) of the registration frame 200 may be tracked in patient space with a tracking system. In some cases, the pose of the registration frame 200 in patient space may be determined by an optical tracking system that uses an optical localizer to detect IR light reflected by one or more of the IR reflectors 208a-208d to determine the pose of the registration frame 200 within patient space. In cases where the registration frame 200 instead uses a different type of tracking device, a corresponding tracking system other than an optical tracking system may be used to determine the pose of the registration frame 200 in patient space.

In cases where the registration frame 200 does not include tracking devices, it is contemplated that the pose of the registration frame 200 in patient space may be determined by a tracking system that does not require tracking devices (for example, a computer vision tracking system that has been trained to use visible light to identify the registration frame 200 and determine its pose within patient space).

Figure 2B:
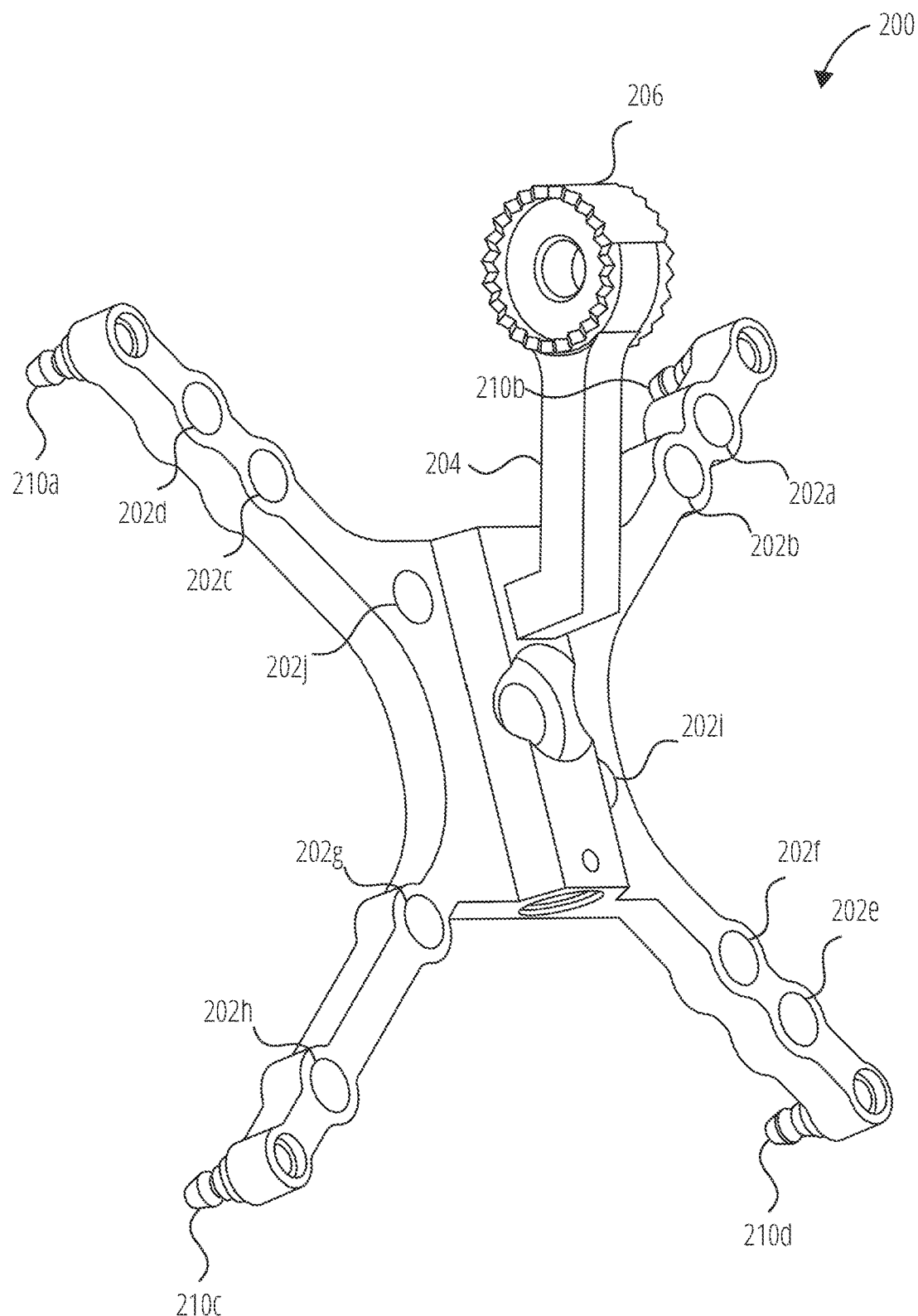
FIG. 2B illustrates a registration frame according to an embodiment.

FIG. 2B illustrates the registration frame 200 according to an embodiment. In FIG. 2B, the IR reflectors 208a-208d have been removed from the registration frame 200, revealing the attachment posts 210a-210d. The registration frame 200 may be configured to receive different tracking devices (other than the IR reflectors 208a-208d) on the attachment posts 210a-210d if the registration frame 200 is to be used with a tracking system that uses such different tracking devices.

The registration frame 200 can be used, via methods disclosed herein, to create a registration of an image space (e.g., corresponding to CT image data, as described above) to the patient space within the navigation system 100. Further, once this registration occurs between the patient space of the patient 102 and image space of the image data via the registration frame 200, the registration frame 200 can be used to maintain the registration.

Figure 3:
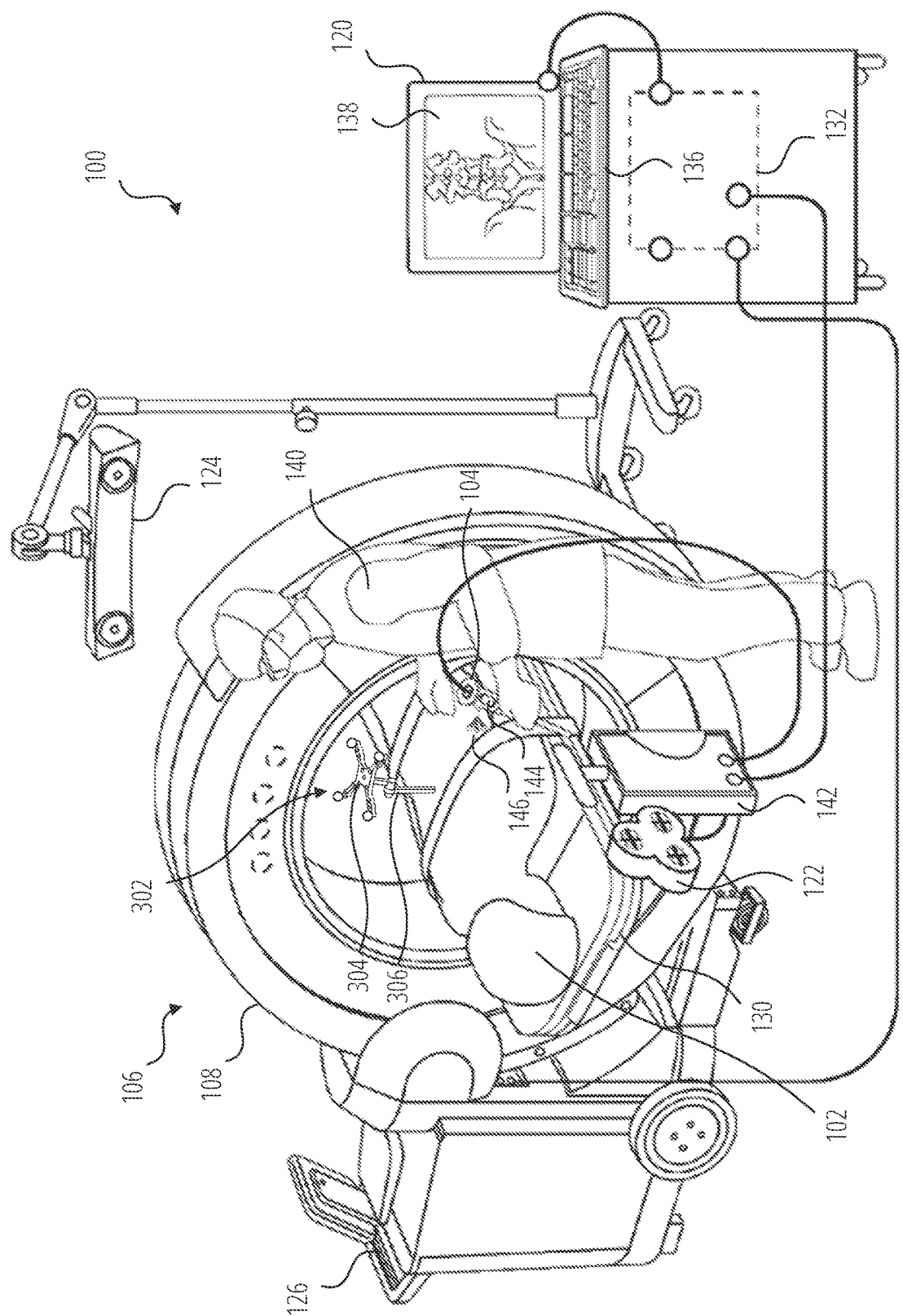
FIG. 3 is a diagrammatic view illustrating an overview of a navigation system that can be used for various procedures, according to various embodiments.

FIG. 3 is a diagrammatic view illustrating an overview of the navigation system 100 that can be used for various procedures. In FIG. 3, a registration frame assembly 302 comprising a registration frame 304 and a fixation portion 306 has been attached (using the fixation portion 306) to the patient 102 (e.g., to a vertebrae of the patient 102). Accordingly, the registration frame 304 presents a fixed position relative to the patient 102.

The fixation portion 306 can be affixed to a portion of the anatomy (as shown in FIG. 3 as attached to the spinal column of the patient 102), or may in other instances be affixed elsewhere within the navigation system 100 to a location that is static relative to the patient 102 (but without necessarily being affixed directly to a portion of the anatomy of the patient 102). This fixation portion 306 may include a clamp or other mechanism in order to allow for such fixation. Accordingly, the registration frame 304 may be present in the patient space in a manner that is static relative to the patient 102.

The navigation system 100 can then begin the process that uses the registration frame 304 to compute a transform between a patient space and an image space. The navigation system 100 may first identify the pose of the registration frame 304 within the patient space using a tracking system, in the manner described above.

The navigation system 100 may also generate image data of the image space corresponding to the patient space using an imaging process. The imaging process may be performed by imaging device 106 (which may be, e.g., a CT imaging device as described above). The imaging device 106 may, as part of the imaging process, image the patient space to generate image data of the image space. This imaging process may result in three dimensional (3D) image data for the image space. This image data may be made up of image volume data arranged in voxels, according to an image voxel scale. The navigation system 100 then takes (or calculates) intensity values for each voxel of the image data.

The image data includes image data for the patient 102 (as would be expected when using the imaging processes as described above). Further, due to the placement of the registration frame 304 within the patient space as illustrated in FIG. 3, the image data taken by the navigation system 100 should also include an image of the registration frame 304.

To reduce computation time for the proceeding steps, the navigation system 100 may crop the portion of the image data that includes the image of the registration frame 304. If the cropping process is successful, the image of the registration frame 304 is used (alone) in certain proceeding steps. If the cropping process is not successful, the image of the registration frame 304 may be used in proceeding steps as contained within the overall image data (which may take a relatively longer amount of time).

To perform the cropping, a cropping threshold is set to a percentage (e.g., 90%) of a maximum intensity value anticipated as possible within the image data (e.g., maximum possible intensity*0.9). In some systems, the maximum anticipated intensity may be, e.g., 4,095. As discussed above, the registration frame 304 may be or include materials that are known to reliably result in high intensity voxels corresponding to the registration frame 304 that are at or above the cropping threshold when the registration frame 304 is imaged. Accordingly, the navigation system 100 may then crop the image data around such voxels that exceed (and/or meet or exceed) the cropping threshold, which is presumably the image of the registration frame 304.

If the image cropping is unsuccessful the first time, the cropping threshold may be set to a lower percentage (e.g., 70%) and the process repeated in order to attempt to crop out the image of the registration frame 304.

In the case of a successful cropping (at whatever point), a cropping transform is recorded to transform back to the original image after certain of the proceeding steps are performed on the cropped out image of the registration frame 304. Further, a padding around the crop of the detected high intensity voxels may be used to ensure the capturing of the image around the registration frame 304. This padding may be, for example, a 20 mm padding, or some other value.

If the cropping is unsuccessful again after these (and potentially other) attempts, the entire image data that includes the image of the registration frame 304 is used instead of the cropped out image of the registration frame 304 in certain proceeding steps, as described.

As a result of the imaging process, the image of the registration frame 304 (whether cropped out or not) has high intensity voxels corresponding to the material of the registration frame (due to the nature of the material of the registration frame as described above) and low intensity voxels corresponding to each of the plurality of apertures of the registration frame (since such apertures do not comprise such material).

The navigation system 100 may then calculate an inverted image of the registration frame 304 having low intensity voxels corresponding to the material of the reference registration frame 304 and high intensity voxels corresponding to each of the plurality of apertures of the reference registration frame 304. To generate the inverted image of the registration frame 304, the navigation system 100 may perform a 3D closing operation on the image of the registration frame 304. In some embodiments, the 3D closing operation is designed to work with gray scale image data. Accordingly, in such embodiments, the image of the registration frame 304 (and/or the rest of the image data that it is located within, if the registration frame 304 has not been cropped out of such image data) is converted to gray scale in order to function with the 3D closing operation.

Then, to perform the 3D closing operation, a kernel may be used which represents the size of the aperture (which in some embodiments may be 5 mm in diameter). This closing operation may proceed to "fill in" the low intensity voxels corresponding to the apertures in the image of the registration frame 304 with high intensity voxels instead. This closing operation results in a closed image of the registration frame 304 having high intensity voxels corresponding to the material of the registration frame and high intensity voxels corresponding to each of the plurality of apertures of the registration frame 304.

The navigation system 100 then may subtract the original image of the registration frame 304 from the closed image of the registration frame 304. The result is the described inverted image of the registration frame 304 having low intensity voxels corresponding to the material of the reference registration frame 304 and high intensity voxels corresponding to each of the plurality of apertures of the reference registration frame 304.

The inverted image of the registration frame 304 may then be converted to a binary image, which converts each of the voxels in the inverted image of the registration frame 304 to one of either the lowest intensity or the highest intensity. This may be done based on a series of multiple thresholds. The threshold values may be determined based on observational results when such thresholds are tested with certain test data. Other thresholds not related to observational data (but which may be theorized to work well in the case that the image data including the image of the registration frame 304 was taken using a scanner not corresponding to the observational results) may also be used. Some thresholds may be based on the assumption that the material of the reference registration frame 304 (e.g., titanium) is represented in a certain intensity value range (e.g., the intensity value range ~1,200-3,000). Other thresholds may be based on a maximum intensity value found in the (inverted) image data being affected, under the assumption that the apertures of the registration frame 304 are probably represented by the upper end of the intensity value range within the (inverted) image data.

For data corresponding to each threshold used, a list of connected component objects representing groupings of high intensity voxels within the inverted image of the registration frame 304 (after adjustment by the threshold as described above) is generated. Using the known size of the apertures, some of the groupings of high intensity voxels found are eliminated (for being the wrong size) and the resulting groupings after this process recorded. The process then repeats, using each of the thresholds on a copy of the inverted image of the registration frame 304.

The remaining aperture candidates (groupings of high intensity voxels) in each copy of the inverted image registration frame 304 after the process completes may be determined to correspond to actual (candidate) aperture locations, and the centroids of these groupings of high intensity voxels are determined and recorded.

Once the candidate aperture locations within the image data are so determined for each copy of the inverted image of the registration frame 304, the navigation system 100 then matches aperture representations of a model of the registration frame to those candidate aperture locations. In the case where the inverted image of the registration frame 304 was generated from a cropped image of the registration frame 304, the cropping transform may be used against the determined locations to determine the aperture locations relative to the image data as a whole as taken by the imaging device.

The model of the registration frame that is used may be a text based model of the registration frame 304. This may mean that the navigation system 100 may be configured to accept a textual information regarding the model and to generate the model itself in real time using the textual information. This process may involve determining the locations and dimensions of portions of the model, such as, for example, bars representing the material of the registration frame 304 within the model and holes representing the apertures of the registration frame 304. In other cases, the model is simply provided to the navigation system 100.

The model so used and/or generated may include various data sets corresponding to the registration frame 304. For example, the navigation system 100 may use the model to determine a data set of nominal aperture centers within the model; a data set of 3D grid points of the model, similar to some computer aided design (CAD) models; and/or a transform from the coordinates used for positioning relative to the model itself (e.g., the model center) to the point on the model that corresponds to the point on the actual registration frame 304 used for locating the registration frame 304 within the patient space.

The nominal aperture centers from the model may be then matched to the candidate aperture locations corresponding to each copy of the inverted image of the registration frame 304. For each set of candidate aperture locations, a total error may be computed between the candidate aperture locations and their corresponding nominal aperture centers within the model. One manner of calculating this total error may be a root-mean-square (RMS) error calculation that compares each candidate aperture location of a set to its corresponding nominal aperture center within the model. The set of candidate aperture locations with the lowest total error corresponding to the model may be selected as the working set of aperture locations within the image space. The fit of the model to this working set of aperture locations accordingly represents the pose of the registration frame 304 within the image space.

The navigation system 100 then computes a transform between the patient space and the image space based on the differences between the pose of the registration frame 304 within the patient space and the pose of the registration frame 304 within the image space.

Other outputs that may be generated by the matching process include values (in image space) for the aperture locations in the working set of aperture locations; values (in patient space) of the working set of aperture locations (as translated into the patient space using the image space values with the transform); the result of the best RMS calculation corresponding to the working set of aperture locations; data showing which nominal aperture centers from the model matched with which aperture locations of the final set of aperture locations within image space; and/or the volume of any given aperture location in the working set of aperture locations as compared to the nominal volume of that aperture within the model. This information may be displayed to the user 140 so the user 140 can ensure that the result of the registration process has reached a reasonable registration result prior to proceeding.

In some embodiments, the transform so computed may be further optimized for additional accuracy. In some examples, the transform may be optimized by checking the symmetry of a representation of an aperture of the plurality of the apertures of the registration frame according to an adjustment of the transform. In some examples, the transform may (additionally or alternatively) be optimized by checking an alignment between a pair of plates of material of the registration frame taken according to an adjustment of the transform. Each of these examples is explained in more detail later in the application.

The transform (whether or not it has been optimized), determined as described above, may be used with another object (e.g., the instrument 104) with a known pose in the patient space (as determined by, e.g., a tracking system as described above) to determine the corresponding pose of the object within the image space. A representation of the object within image space corresponding to that image space pose may then accordingly be displayed on, for example, the display device 120 by the navigation system 100. In this fashion, it can be said that the generation and use of this transform registers the patient space to the image space, or registers the patient space and the image space together.

Figure 4:
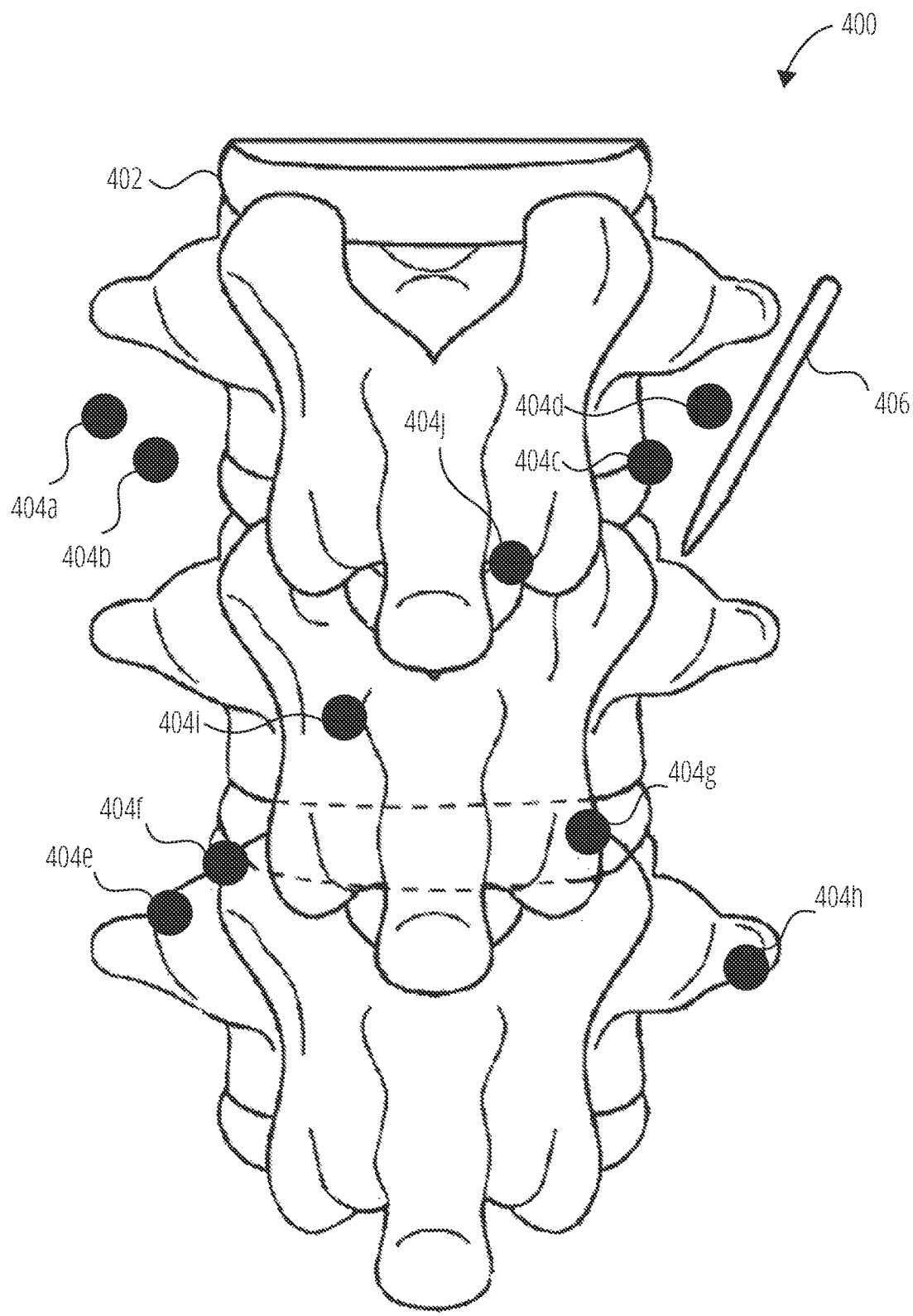
FIG. 4 illustrates image data corresponding to image space near a patient and the use of a transform to provide for the representation of an instrument found in patient space within the image data corresponding to the image space, according to an embodiment.

FIG. 4 illustrates image data 400 corresponding to image space near the patient 102 and the use of a transform to provide for the representation 406 of an instrument found in patient space within the image data 400 corresponding to the image space, according to an embodiment. All or part of the image data 400 may be displayed on, e.g., the display device 120 of the navigation system 100.

The image data 400 may include the spinal column 402 of the patient 102, as it is found in image space. The spinal column 402 may be present in the image data 400 as a result of an imaging by an imaging device, as described above.

In the image data 400, the aperture locations 404a-404j within the image data may be illustrated within the current top-down view of the spinal column 402 in image space, as shown. These aperture locations 404a-404j may have been determined in the manner described above. Based on a comparison of the apparent positioning of the registration frame 304 within the patient space (shown in FIG. 3), it can be seen that the aperture locations 404a-404j are located in the image space in corresponding locations.

It may be that in some cases the aperture locations 404a-404j as calculated as described above are (or are not) so illustrated in the image data 400 based on the needs of the user 140. For example, the display of the aperture locations 404a-404j may be useful for the user 140 to double check that the navigation system 100 has apparently properly identified the aperture locations 404a-404j correctly/reasonably as compared to the location of the registration frame 304 in the patient space. In other cases, the user 140 may not wish for the aperture locations 404a-404j to be illustrated in the image data 400, and may instruct the navigation system 100 to remove them (or not display them in the first instance). In other cases, the aperture locations 404a-404j may not be illustrated by default, but are simply used by the navigation system 100 in the manner described above.

The image data 400 further comprises the representation 406. The representation 406 may correspond to, e.g., the instrument 104 of FIG. 3. When the user 140 poses the instrument 104 in patient space, the navigation system 100 may track the pose of the instrument 104 in patient space, as described above. Then, using the transform, the navigation system 100 may determine the corresponding pose of the instrument 104 within the image space. The navigation system 100 may then provide a representation 406 of the instrument 104 corresponding to this image space pose in the image data 400, as illustrated.

The user 140 can view a reproduction of all or part of the image space on, for example, the display device 120 and determine just where the instrument 104 is in relation to the various portions of the spinal column 402 (which may be internal to the patient 102 in the patient space and therefore not visible in the patient space). It may be that only a portion or portions of the image data 400 (which is three dimensional) is displayed on the display device 120 at a time. The portions of the spinal column 402, the aperture locations 404a-404j (if present in the image data 400), and/or the representation 406 (e.g., of a tracked object) may be illustrated as they intersect/apply to, for example, a two dimensional plane sliced from the image data 400 that is displayed on, for example, the display device 120. Multiple simultaneous such planes (for example, from different approaches in the patient space) may be displayed at once by the navigation system 100 on the display device 120 or another display device (not illustrated).

As described, this registration is accomplished automatically at the navigation system 100. For example, the registration is accomplished without the user 140 having to themselves perform any express synchronization action(s) to allow the navigation system 100 to extrapolate a transform between patient space and image space, but rather is accomplished simply by the placement of the registration frame assembly 302 within the patient space as described, and perhaps a simple instruction to the navigation system 100 (e.g., via the user interface 136) to perform the registration process as described. This "automatic" registration reduces the training burden for the user 140 as to other, more complicated registration methods, and removes potential avenues of error that could be made by the user 140 when using those more complicated registration methods. Further, the use by the system of apertures on the registration frame 304 (rather than, e.g., fiducials, materials differences, etc., on and/or internal to the registration frame 304) minimizes burdens and costs corresponding to the manufacture of the registration frame 304, as the apertures within the registration frame 304 (which may be, e.g., a metal such as titanium) can be straightforwardly provided for using an accurate mold corresponding to the form of the registration frame 304.

Figure 5:
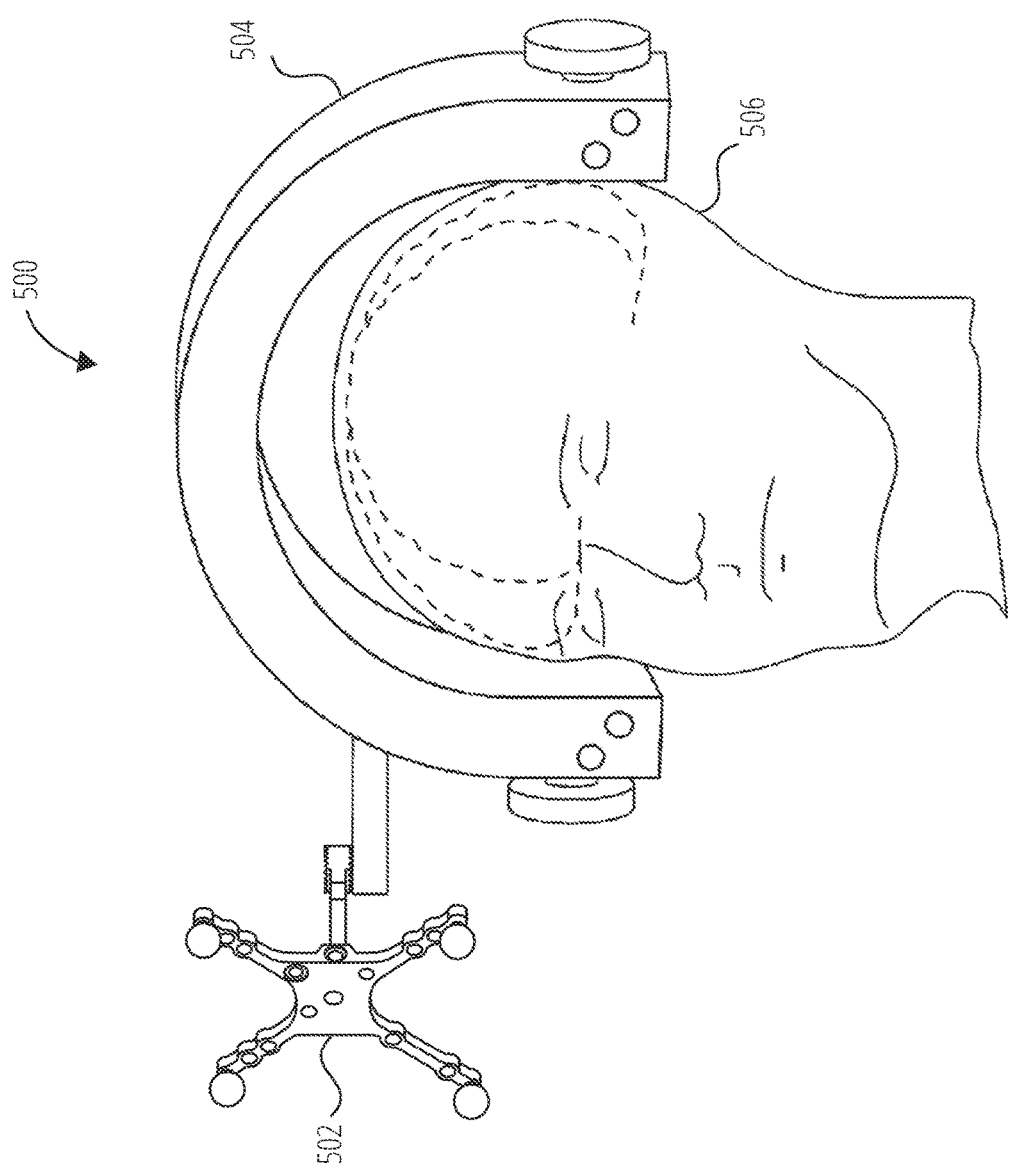
FIG. 5 illustrates the use of an apparatus comprising a registration frame and a patient fixation device with a patient, according to an embodiment.

FIG. 5 illustrates the use of an apparatus 500 comprising a registration frame 502 and a patient fixation device 504 with a patient 506, according to an embodiment. In certain embodiments involving the use of the registration method described above, the registration frame 502 is held static relative to a part of the patient 506 that is not the spinal column. In the case of FIG. 5, the registration frame 502 is held static relative to the head of the patient 506 though its attachment to the patient fixation device 504 that is holding the head of the patient 102 in place. This arrangement may be attendant to a procedure to be performed on, for example, the brain of the patient. Accordingly, an imaging device may take an image of the head of the patient 506 that also captures some or all of the registration frame 502, in the manner described above.

Figure 6:
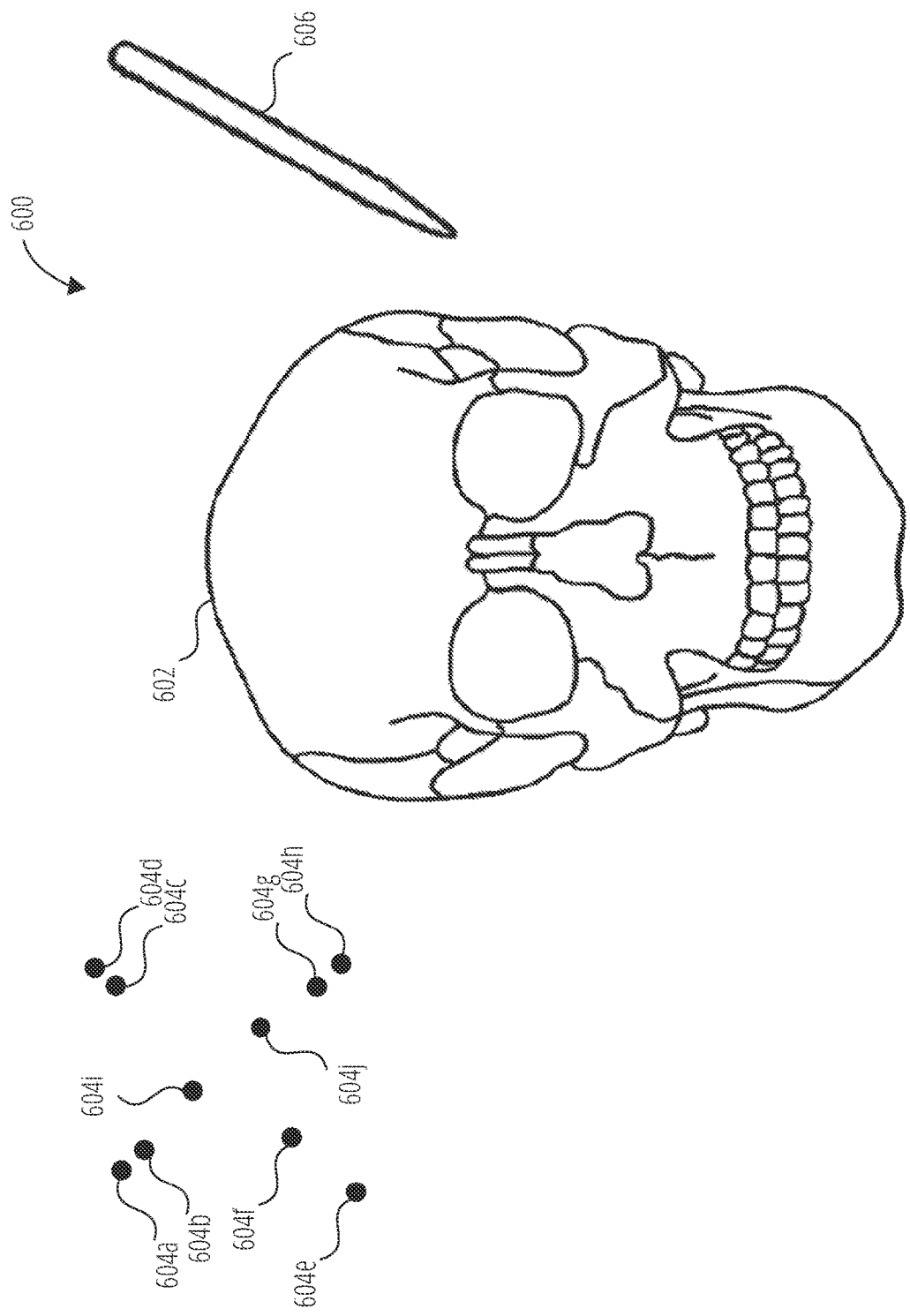
FIG. 6 illustrates image data corresponding to image space near the patient and the use of a transform to provide for the representation of an instrument found in patient space within the image data corresponding to the image space, according to an embodiment.

The method described in FIG. 5 above may then be used to determine a transform between the patient space and the image space such that an object (such as an instrument used for brain surgeries) can be tracked in image space. FIG. 6 illustrates image data 600 corresponding to image space near a patient and the use of a transform to provide for the representation 606 of an instrument found in patient space within the image data 600 corresponding to the image space, according to an embodiment. All or part of the image data 600 may be displayed on, e.g., the display device 120 of the navigation system 100 (assuming that the patient 102 has been swapped for the patient 506).

The image data 600 may include the head 602 of the patient 506, as it is found in image space. The head 602 may be present in the image data 600 as a result of an imaging by an imaging device, as described above.

In the image data 600, the aperture locations 604a-604j within the image data may be illustrated within the face-on view of the head 602 in image space, as shown. These aperture locations 604a-604j may have been determined using the methods described above. Based on a comparison of the apparent positioning of the registration frame 502 within the patient space (shown in FIG. 5), it can be seen that the aperture locations 604a-604j are located in the image space in corresponding locations. As before, these aperture locations 604a-604j may or may not be expressly illustrated in the image space.

A transform between the patient space and the image space may be calculated based on a matching of a model of the registration frame 502 to the aperture locations 604a-604j to determine a pose of the reference registration frame 502 in image space, and then comparing a pose of the registration frame 502 in patient space with the pose of the registration frame 502 in image space, in the manner described above.

The image data 600 further comprises the representation 606. The representation 606 may correspond to, e.g., an instrument (such as the instrument 104 of FIG. 3), and the pose of representation 606 may match/correspond to a pose of the instrument in the patient space, as determined through use of the transform between the patient space and the image space.

All or portion(s) of the image data 600, including any relevant portions of the head 602, the aperture locations 604a-604j (if present in the image data 600) and/or the representation 606 may be illustrated for use by the user 140, analogous to the manner described above.

Figure 7:
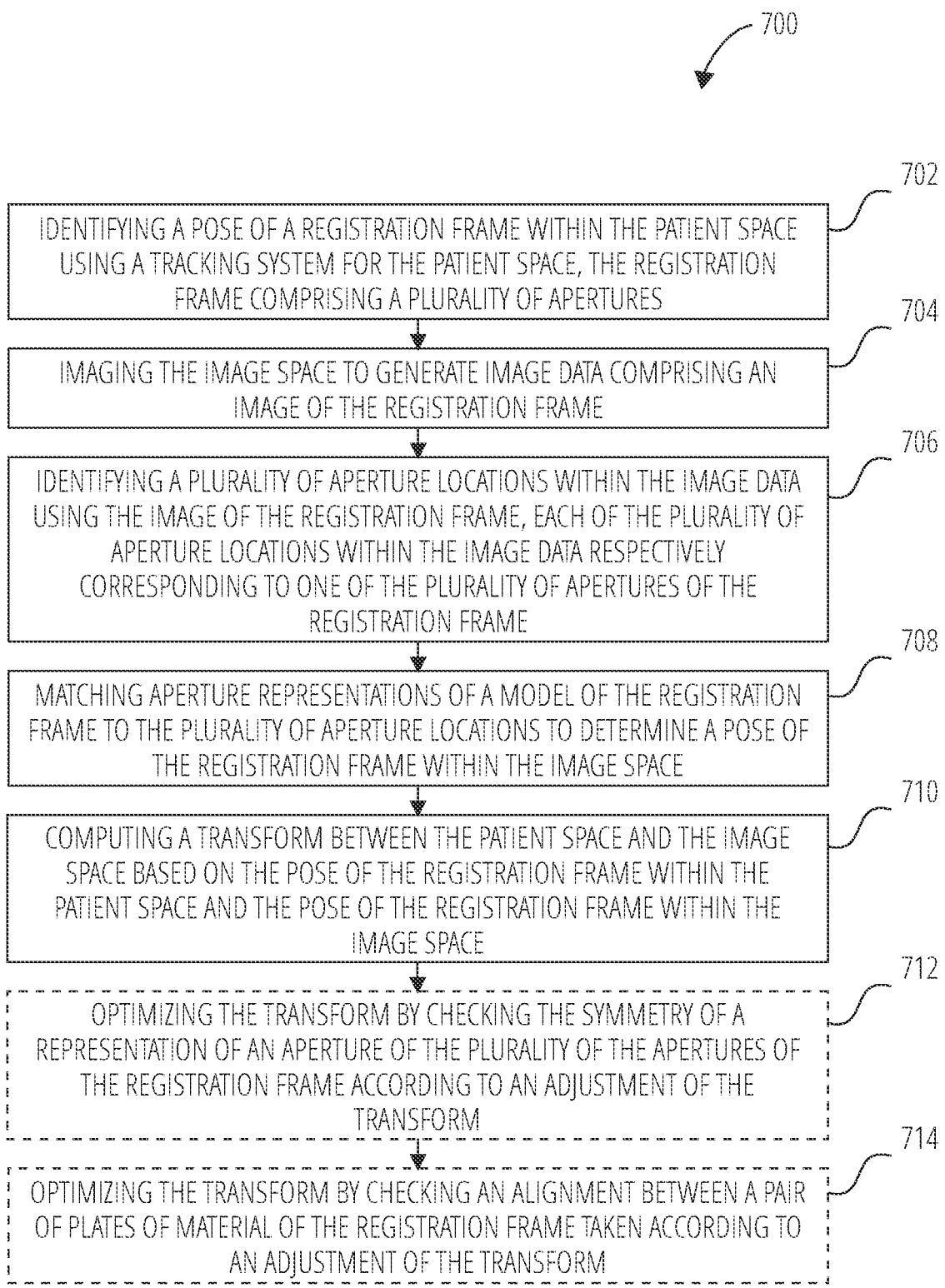
FIG. 7 illustrates a method of registering a patient space and an image space, according to an embodiment.

FIG. 7 illustrates a method 700 of registering a patient space and an image space, according to an embodiment. The method 700 includes identifying 702 a pose of a registration frame within the patient space using a tracking system for the patient space, the registration frame comprising a plurality of apertures.

The method 700 further includes imaging 704 the image space to generate image data comprising an image of the registration frame.

The method 700 further includes identifying 706 a plurality of aperture locations within the image data using the image of the registration frame, each of the plurality of aperture locations within the image data respectively corresponding to one of the plurality of apertures of the registration frame.

The method 700 further includes matching 708 aperture representations of a model of the registration frame to the plurality of aperture locations to determine a pose of the registration frame within the image space.

The method 700 further includes computing 710 a transform between the patient space and the image space based on the pose of the registration frame within the patient space and the pose of the registration frame within the image space.

The method 700 further optionally includes optimizing 712 the transform by checking the symmetry of a representation of an aperture of the plurality of the apertures of the registration frame according to an adjustment of the transform.

The method 700 further optionally includes optimizing 714 the transform by checking an alignment between a pair of plates of material of the registration frame taken according to an adjustment of the transform.

Figure 8:
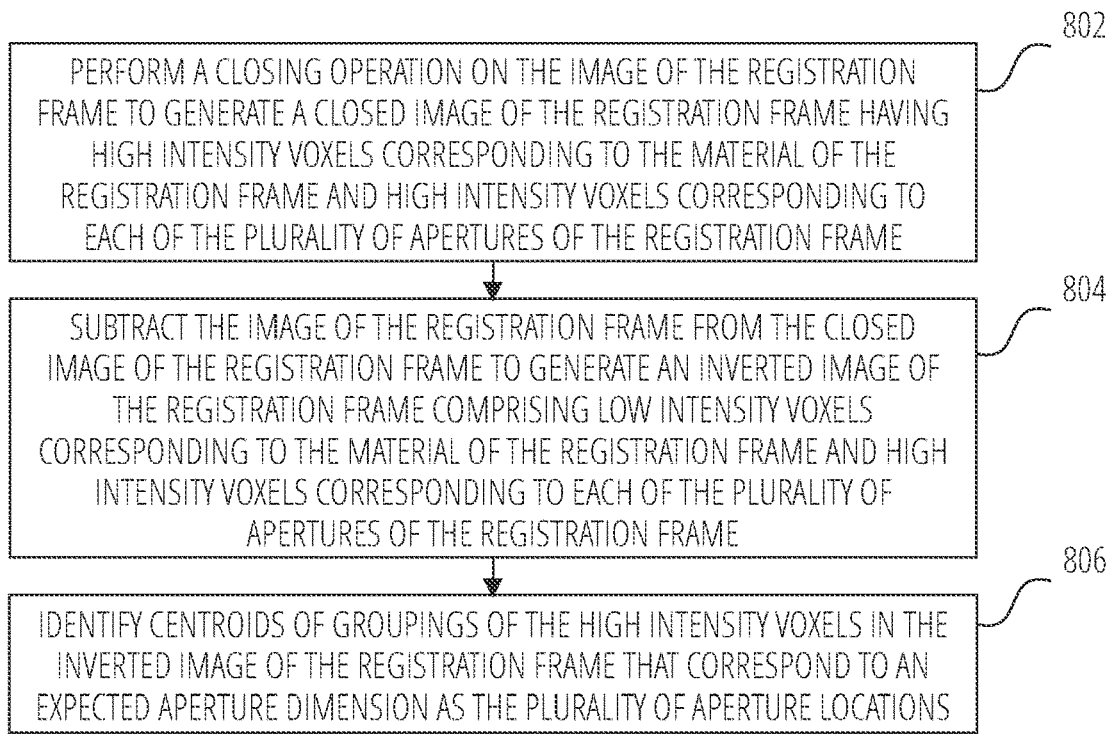
FIG. 8 illustrates a method of identifying a plurality of aperture locations within an image of a registration frame found in image data, according to an embodiment.

FIG. 8 illustrates a method 800 of identifying a plurality of aperture locations within an image of a registration frame found in image data, according to an embodiment. In the embodiment corresponding to FIG. 8, the image of the registration frame has high intensity voxels corresponding to the material of the registration frame and low intensity voxels corresponding to each of a plurality of apertures of the registration frame.

The method 800 includes performing 802 a closing operation on the image of the registration frame to generate a closed image of the registration frame having high intensity voxels corresponding to the material of the registration frame and high intensity voxels corresponding to each of the plurality of apertures of the registration frame.

The method 800 further includes subtracting 804 the image of the registration frame from the closed image of the registration frame to generate an inverted image of the registration frame comprising low intensity voxels corresponding to the material of the registration frame and high intensity voxels corresponding to each of the plurality of apertures of the registration frame.

The method 800 further includes identifying 806 centroids of groupings of the high intensity voxels in the inverted image of the registration frame that correspond to an expected aperture dimension as the plurality of aperture locations.

It is further contemplated that the transform generated using the methods described above may be further optimized after it is generated (and perhaps prior to its use in forming a representation of an object in patient space in the image space attendant to, e.g., a surgical procedure). Such a transform prior to optimization may be discussed herein relative to optimization processes as a "working transform."

Methods of optimizing such a working transform may first involve receiving image data that includes an image of the registration frame and proceeding to crop out the image of the registration frame using the working transform. This may be accomplished by using a padding value with the crop in order to ensure that the entire image of the registration frame is captured. In some embodiments, the padding may be 20 mm. Other values are contemplated.

These methods of optimization may also use the values in image space for the aperture locations in the working set of aperture locations and their corresponding values in patient space, as described above.

These methods may perform optimization with the cropped image of the registration frame through the use of a plurality of initial parameter sets. In some embodiments, each such initial parameter set consists of three values. The first value represents a rotation in x, the second value represents a rotation in y, and the third value represents a translation in z. Accordingly, each initial parameter set defines a theoretical change to the current working transform as defined by these rotation and translation values.

Some initial parameter sets may be generated by repeating registration processes discussed above, but by using fewer holes (e.g., one fewer). For instance, after centroids of groupings of the high intensity voxels in an inverted image of the registration frame are identified as the plurality of aperture locations, the model of the registration frame could be matched to the set containing fewer of such aperture locations. This repeated matching using fewer locations may be repeated to generate a plurality of secondary transforms, which may be slightly different than the working transform and from each other (because of the differing sets of aperture locations that were matched to). The differences between each of these secondary transforms and the working transform in rotation in x, rotation in y, and translation in z may then be calculated for each of this plurality of secondary transforms, with each set of such values corresponding to a secondary transform being saved as a parameter set.

It is also contemplated that additional initial parameter sets could be generated in other ways. For example, parameter sets may be generated based on pre-determined stepping amounts in each of rotation in x, rotation in y, and translation in z. It is contemplated that in the case of multiple available methods of optimization of the working transform, each of these stepping amounts may be adjusted relative to adjustment parameters corresponding to the optimization method when being used with such an optimization method in order to generate each of these initial parameter sets.

Once the described parameter sets are determined (in whatever fashion), outliers may be removed. Outliers of the parameter sets may be identified using a root-sum-squared method that determines that a parameter set is an outlier if it is more than, for example, 10 times (or some other multiple of) a resulting median value of the population of the rest of the parameter sets.

Remaining parameter sets are then saved as the plurality of initial parameter sets to be used in processes described below.

Methods of optimization may use a Nelder-Mead optimization method with the plurality of initial parameter sets in order to identify a best modification to the working transform. Steps that are common as between multiple such optimizations using Nelder-Mead will now be discussed.

A cost function (corresponding to the kind of optimization being run) is identified. Then, for each of the initial parameters, the working transform is adjusted by the initial parameter to generate an adjusted transform. The cropped image of the registration frame (which was taken using the unadjusted working transform) is then analyzed according to each of these adjusted transforms in order to calculate a cost value associated with that adjusted transform (with the nature of the analysis being specific to the optimization method being used). This cost value thus corresponds to the initial parameter set used to generate the used adjusted transform.

Because the cropped image of the registration frame is three-dimensional, the Nelder-Mead based optimization method selects the four initial parameter sets that correspond to the four lowest calculated costs. The Nelder-Mead optimization is then implemented (using the same cost function that was used to determine the four closest parameter sets) to optimize between this sub-plurality of the plurality of initial parameters. The Nelder-Mead iterates by replacing one of the four (current) parameter sets (whether initial or previously used to replace) with a candidate parameter set near (e.g., extrapolated from) the four current parameter sets that is found to have an even lower calculated cost when using its corresponding adjusted transform to analyze the cropped image of the registration frame (again, the nature of the analysis is specific to the optimization method being used). A number of iterations of this process may occur (90 is contemplated) to swap through candidate parameter sets. After all iterations are complete, a final parameter set corresponding to the lowest calculated cost value seen during the operation remains.

This final parameter set (in rotation in x, rotation in y, and translation in z) is then applied to the working transform to generate an optimized transform.

A first optimization method using Nelder-Mead in the manner described above assumes that the cropped image of the registration frame is symmetrical relative to the center line in the depth (z) direction. Then for each adjusted transform, multiple cross-sections ("plates") of the cropped image of the registration frame (which was taken using the unadjusted working transform), according to the adjusted transform, are taken. The multiple cross-sections may be taken at different depths to give multiple plates. This will essentially result in a point cloud of pixels for each plate, each point having an intensity (e.g., based on whether it represents material, an aperture, or an edge pixel).

The plates may be generated corresponding to the size of the frame. For example (and not by way of limitation), plates from −3.5 mm to 3.5 mm in increments of 0.05 mm may be generated when using a frame that is 5 mm thick. The plates generated that are outside the registration frame may provide a black background that helps to drive the method to a faster and better optimization.

The plates are then divided into "top" and "bottom" such plates (determined as you pass through the cropped image of the registration frame in the z direction, relative to an x-y plane passing through the center of the cropped image of the registration frame).

These plates are then analyzed according to the cost function:

$$\sum_{i=1}^{N}\sum_{j=1}^{P}|T_{ij}-B_{ij}|, \text{ where:}$$

N is the number of top plates (or bottom plates);
P is the total number of pixels at a given plate 'i';
$T_{ij}$ is the intensity value of the top plate 'i' and pixel 'j'; and
$B_{ij}$ is the intensity value of the bottom plate 'i' and pixel 'j'.

The general principle of this cost function is that, again assuming that the cropped image of the registration frame is symmetrical relative to the center line in the depth (z) direction, the corresponding best transform that makes this assumption hold true should correspond to very small (effectively zero) differences between a top plate and its corresponding bottom plate taken according to such a transform, due to the orthogonal (to the x-y plane) nature of the apertures in the registration frame.

The initial parameter sets that generate adjusted transforms that, when used to pull plates from the cropped image of the registration frame, result in the four lowest cost values calculated using the above cost function are selected for use with the Nelder-Mead process. The Nelder-Mead optimization then proceeds as described above, using this cost function, by identifying candidate parameter sets extrapolated using the four (current) parameter sets (whether initial or previously used to replace), generating adjusted transforms according to those parameter sets, calculating associated cost values, and replacing (current) parameter sets (whether initial or previously used to replace) until the process terminates. The final candidate set (the one with the lowest error) is then used to adjust the working transform into an optimized transform.

This first optimization method may be or correspond to optimizing a transform by checking an alignment between a pair of plates of material of the registration frame taken according to an adjustment of the transform.

A second optimization method using Nelder-Mead in the manner described above assumes that the images of the apertures in the cropped image of the registration frame are symmetrical relative to the axis of the apertures. Accordingly, this optimization may work in embodiments where the apertures of the registration frame are in fact symmetrical relative to the axis of the apertures (such as the cylindrical apertures described herein, but other possibilities, such as apertures in the shapes of right prisms with symmetrical face polygons, are contemplated).

Then for each adjusted transform, aperture representations of a model (e.g., the model used in the matching process described above) of the registration frame are imposed on the cropped image of the registration frame (which was taken using the unadjusted working transform) according to the adjusted transform.

Voxels at these imposed locations are then analyzed using the following cost function:

$$\sum_{i=1}^{N}\sum_{j=1}^{P}|L_{ij}-R_{ij}|, \text{ where:}$$

N is the number of apertures in the cropped image of the registration frame;
P is the total number of voxels in half an aperture;
$L_{ij}$ is the intensity value of voxel 'j' in hole 'i' inside one half of the aperture (0°~180°); and
$R_{ij}$ is the intensity value of corresponding voxel 'j' in hole 'i' inside the other half of the aperture)(180°-360°.

The general principle of this cost function is that, again assuming that the images of the apertures in the cropped image of the registration frame are symmetrical relative to the axis of the apertures, the corresponding best transform that makes this assumption hold true should correspond to very small (effectively zero) differences between intensities of a voxel in one half of the aperture and its corresponding voxel in the other half of the aperture, due to the orthogonal (to the x-y plane) nature of the (symmetrical) apertures in the registration frame.

The initial parameter sets that generate adjusted transforms that, when used to impose aperture representations on the cropped image of the registration frame, result in the four lowest cost values calculated using the above cost function are selected for use with the Nelder-Mead process. The Nelder-Mead optimization then proceeds as described above, using this cost function, by identifying candidate parameter sets extrapolated using the four (current) parameter sets (whether initial or previously used to replace), generating adjusted transforms according to those parameter sets, calculating associated cost values, and replacing (current) parameter sets (whether initial or previously used to replace) until the process terminates. The final candidate set (the one with the lowest error) is then used to adjust the working transform into an optimized transform.

This second optimization method may be or correspond to optimizing a transform by checking the symmetry of a representation of an aperture of the plurality of the apertures of the registration frame according to an adjustment of the transform.

It is contemplated that in some embodiments, multiple optimization methods may be used. For example, a working transform may be optimized using the first transform optimization method (using plates) as described above. The optimized transform so generated may then be used as the working transform that is used with the second transform optimization method (using aperture representations) as described above. The reverse order is also contemplated. Further, it is understood that additional methods could be so chained if/as they are developed.

Figure 9:
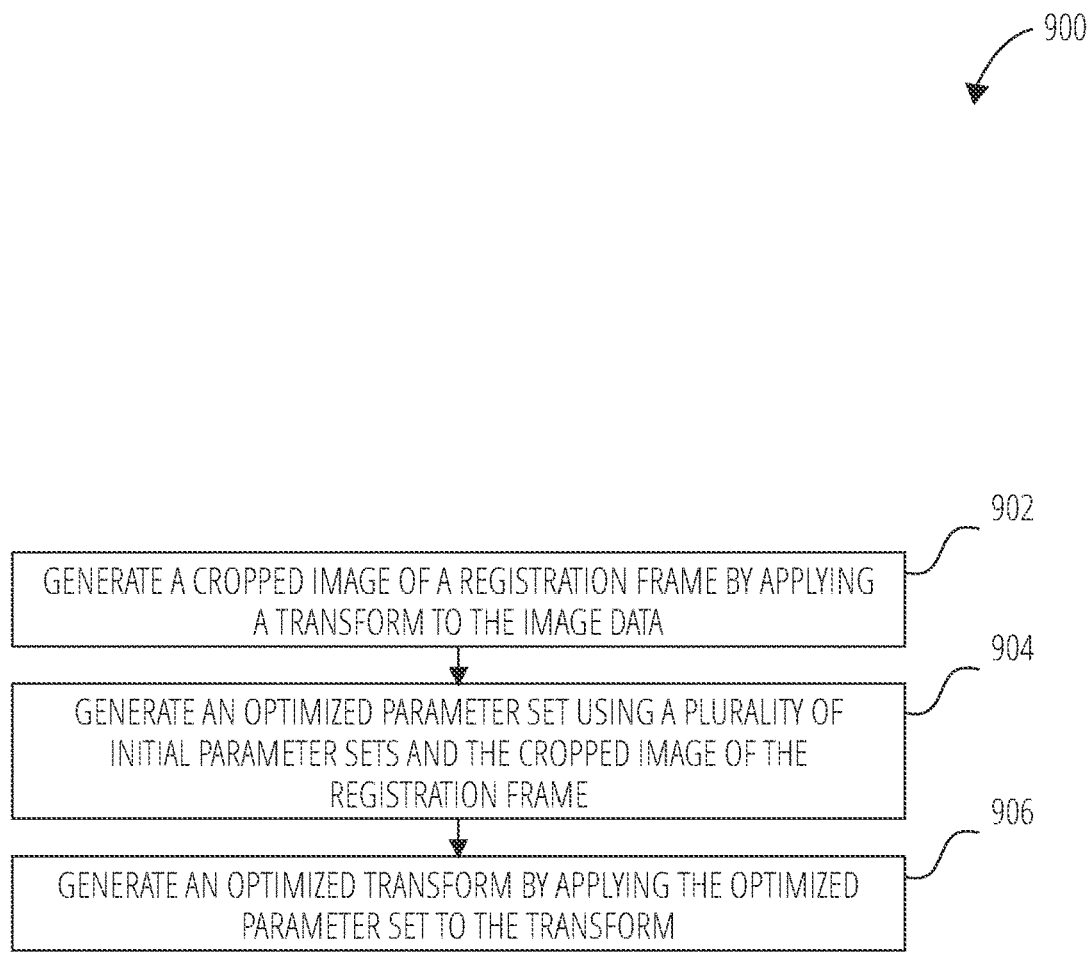
FIG. 9 illustrates a method of generating an optimized transform, according to an embodiment.

FIG. 9 illustrates a method 900 of generating an optimized transform, according to an embodiment. The method 900 includes generating 902 a cropped image of a registration frame by applying a transform to the image data.

The method 900 further includes generating 904 an optimized parameter set using a plurality of initial parameter sets and the cropped image of the registration frame.

The method 900 further includes generating 906 an optimized transform by applying the optimized parameter set to the transform.

Figure 10:
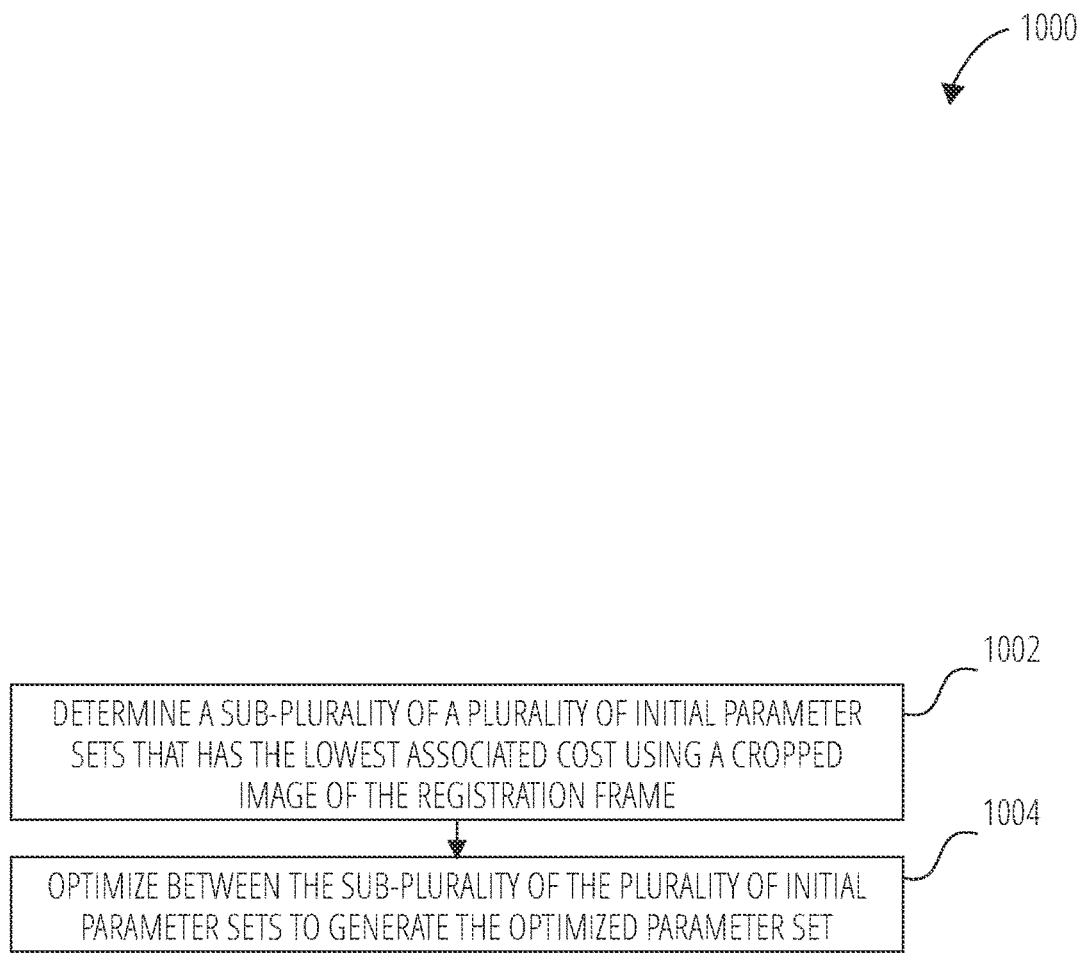
FIG. 10 illustrates a method of generating an optimized parameter set using a plurality of initial parameter sets with a cropped image of a registration frame, according to an embodiment.

FIG. 10 illustrates a method 1000 of generating an optimized parameter set using a plurality of initial parameter sets with a cropped image of a registration frame, according to an embodiment. The method 1000 includes determining 1002 a sub-plurality of a plurality of initial parameter sets that has the lowest associated cost using a cropped image of the registration frame.

The method 1000 further includes optimizing 1004 between the sub-plurality of the plurality of initial parameter sets to generate the optimized parameter set.

Figure 11:
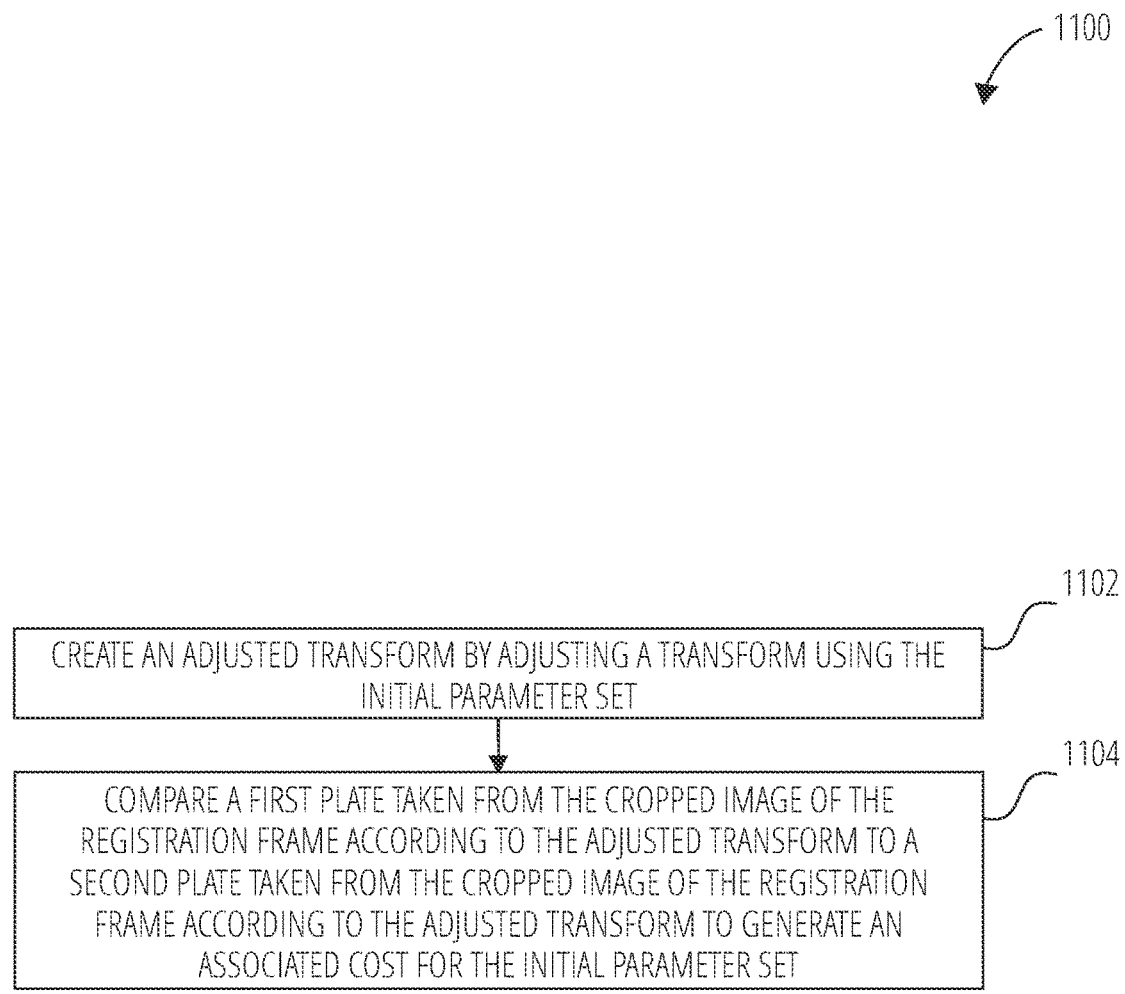
FIG. 11 illustrates a method for determining a sub-plurality of a plurality of initial parameter sets that has the lowest associated cost using a cropped image of the registration frame, according to an embodiment.

FIG. 11 illustrates a method 1100 for determining a sub-plurality of a plurality of initial parameter sets that has the lowest associated cost using a cropped image of the registration frame, according to an embodiment. The method 1100 may be performed on each parameter set in the plurality of initial parameter sets in order to make the determination.

The method 1100 includes creating 1102 an adjusted transform by adjusting a transform using an initial parameter set.

The method 1100 further includes comparing 1104 a first plate taken from the cropped image of the registration frame according to the adjusted transform to a second plate taken from the cropped image of the registration frame according to the adjusted transform to generate an associated cost for the initial parameter set.

Figure 12:
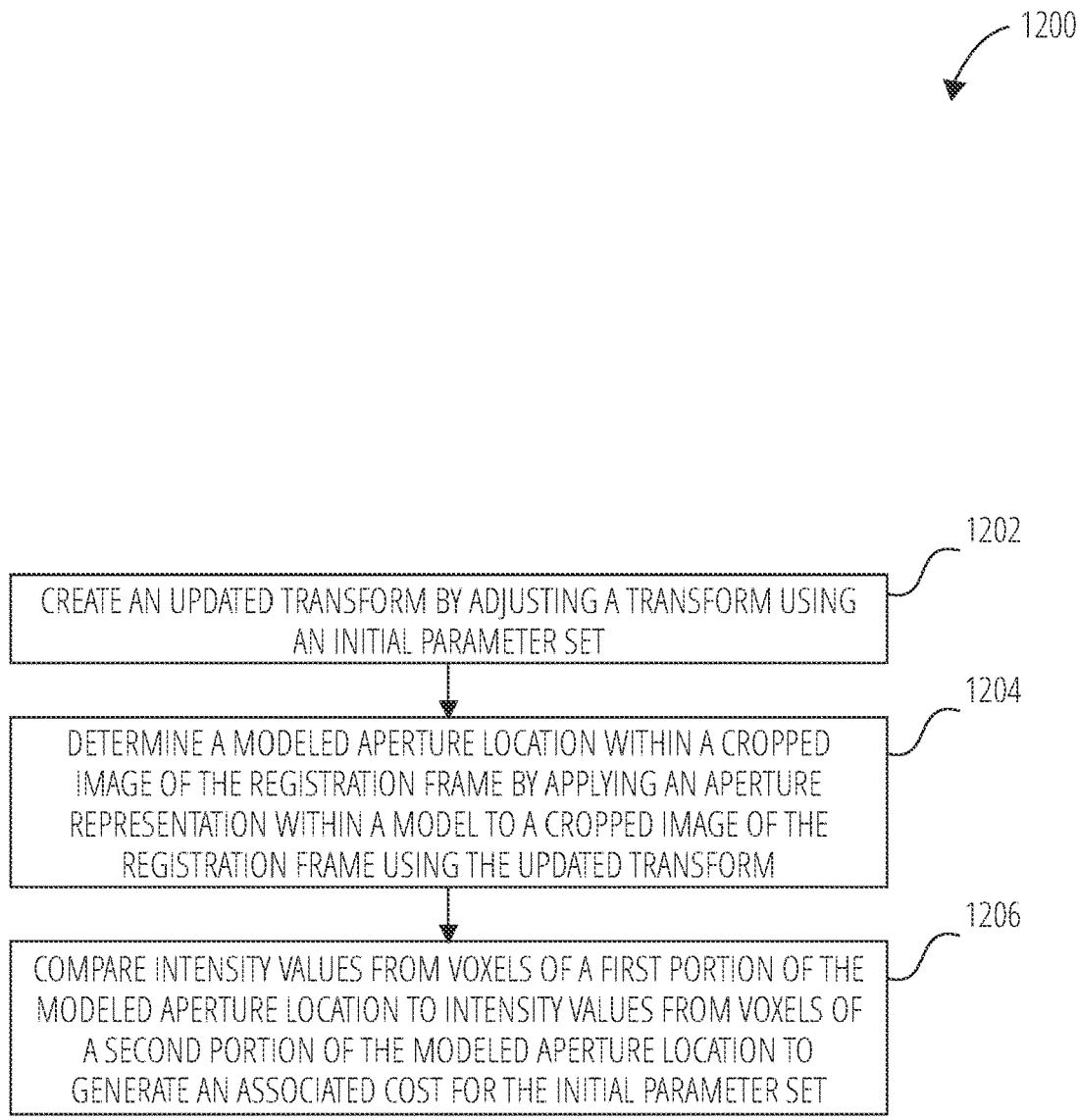
FIG. 12 illustrates a method for determining a sub-plurality of a plurality of initial parameter sets that has the lowest associated cost using a cropped image of the registration frame, according to an embodiment.

FIG. 12 illustrates a method 1200 for determining a sub-plurality of a plurality of initial parameter sets that has the lowest associated cost using a cropped image of the registration frame, according to an embodiment. The method 1200 may be performed on each parameter set in the plurality of initial parameter sets in order to make the determination.

The method 1200 includes creating 1202 an updated transform by adjusting a transform using an initial parameter set.

The method 1200 further includes determining 1204 a modeled aperture location within a cropped image of the registration frame by applying an aperture representation within a model to a cropped image of the registration frame using the updated transform.

The method 1200 further includes comparing 1206 intensity values from voxels of a first portion of the modeled aperture location to intensity values from voxels of a second portion of the modeled aperture location to generate an associated cost for the initial parameter set.

Figure 13:
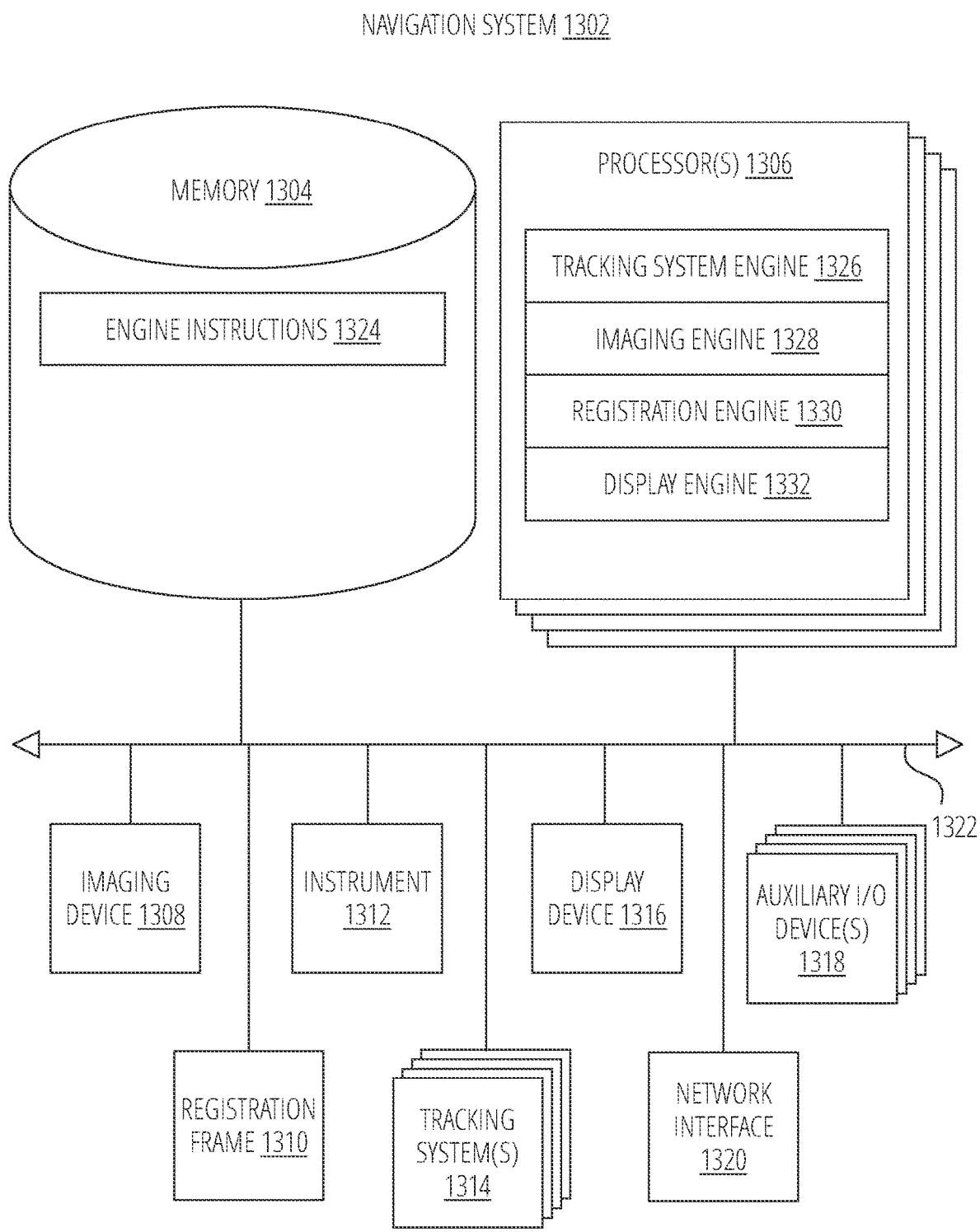
FIG. 13 illustrates the components of a navigation system according to some embodiments.

FIG. 13 illustrates the components of a navigation system 1302 according to some embodiments. The navigation system 1302 includes a memory 1304, one or more processor(s) 1306, an imaging device 1308, a registration frame 1310, an instrument 1312, one or more tracking system(s) 1314, a display device 1316, one or more auxiliary I/O device(s) 1318, and a network interface 1320. Each of these elements may be electronically coupled by a communication interface 1322, which may represent one or more internal communications interfaces (such as, for example, one or more traditional data busses between, e.g., the memory 1304, the processor(s) 1306, and the network interface 1320) and/or one or more external communications interfaces (such as external data wiring to, e.g., the imaging device 1308, one or more tracking system(s) 1314, the display device 1316, and/or one or more of the auxiliary I/O device(s) 1318). Other arrangements are contemplated.

The memory 1304 includes the engine instructions 1324, which may be executed by the one or more processor(s) 1306.

The processor(s) 1306 may operate computer-readable instructions found at the memory 1304 of the navigation system 1302 to perform the various functions thereof as engines. For example, the processor(s) 1306 may operate (execute) the tracking system engine 1326, the imaging engine 1328, the registration engine 1330, and/or the display engine 1332. These instructions may be executed as found in, for example, the memory 1304 of the navigation system 1302 (e.g., in the engine instructions 1324).

The imaging device 1308 may be capable of taking image data corresponding to an image space, in the manner described above. This image data may include, for example, all or part of the registration frame 1310, in the manner described above. This image data may be provided to, e.g., the memory 1304 for storage and/or to the one or more processor(s) 1306 for processing.

The registration frame 1310 may be a registration frame having apertures that may be tracked in patient space by the tracking system(s) 1314, in the manner described above.

The instrument 1312 may be an instrument with one or more tracking devices for use with one or more of the tracking system(s) 1314 to track the instrument 1312 in patient space, as described above.

The tracking system(s) 1314 may be capable of tracking the registration frame 1310 in patient space, in the manner described above. The tracking system(s) 1314 may also be able to track the instrument 1312 (or other object) in the patient space, in the manner described above. The poses of these objects in the patient space may be provided to, e.g., the memory 1304 for storage and/or to the one or more processor(s) 1306 for processing. The tracking system(s) 1314 may include an optical tracking system or some other tracking system.

The display device 1316 may be able to display image data corresponding to the image space. This image data may include one or more portions of a patient as imaged by the imaging device 1308. The display device 1316 may also be able to display a representation of the instrument 1312 or other object within the image space that corresponds to its location in patient space as determined by a transform between the patient space and the image space, as described herein.

The auxiliary I/O device(s) 1318 may provide a way for a local user to provide input/receive output from the system. Examples of such auxiliary I/O device(s) 1318 may include a keyboard, a mouse, a monitor, a speaker, etc. Any results determined by the navigation system 1302 as described herein (e.g., data explaining a pose of a registration frame 1310 in patient space and/or image space, and/or an illustration of aperture locations corresponding to the registration frame 1310 in image space) may be communicated to a user of the navigation system 1302 via the one or more auxiliary I/O device(s) 1318.

The network interface 1320 may transport data into and out of the navigation system 1302. For example, any results determined by the navigation system 1302 as described herein (e.g., data explaining a pose of the registration frame 1310 in patient space and/or image space, and/or an illustration of the registration frame 1310 in image space) may be transported to another device via the network interface 1320. Further, it is anticipated that in some embodiments, the imaging device 1308 and/or the tracking system(s) 1314 may not directly be elements of the navigation system 1302 as illustrated in FIG. 13, but rather may be separate entities that communicate with the navigation system 1302 via the network interface 1320. In this case, the navigation system 1302 may communicate with and use either/both of the imaging device 1308 and/or the tracking system(s) 1314 via the network interface 1320.

The engine instructions 1324 may include instructions for one or more engines, including the tracking system engine 1326, the imaging engine 1328, the registration engine 1330, and/or the display engine 1332. Various ones of these engines may be active within the navigation system 1302 at different times, as the processor(s) 1306 operate(s) the relevant instructions thereof by using the engine instructions 1324.

The tracking system engine 1326 may be configured to track objects (such as the registration frame 1310 and/or the instrument 1312 or other tracked object) in patient space and determine their poses. For example, the tracking system engine 1326 may use the tracking system(s) 1314 to perform these functions. These poses may then be used for registration purposes, in the manner described above.

The imaging engine 1328 may be configured to generate image data corresponding to an image space. The imaging engine 1328 may use the imaging device 1308 to perform this function. Such image data may include an image of all or a portion of the registration frame 1310, in the manner described above. This image data may then be used for registration purposes, in the manner described above.

The registration engine 1330 may be configured to use the poses determined by the tracking system engine 1326 and the image data generated by the imaging engine 1328 to generate a transform between the patient space and the image space, in the manner described above. In some embodiments, the registration engine 1330 may also perform one or more optimization methods on the transform, as described above. The registration engine 1330 may also determine the location to place a representation of a tracked object within image space by using the transform, in the manner described above.

The display engine 1332 may be configured to drive the display device 1316 to display all or part of the image data corresponding to the image space (including a representation of a tracked object within image space) in the manner described above.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. Accordingly, the present embodiments are to be considered illustrative and not restrictive, and the description is not to be limited to the details given herein, but may be modified within the scope and equivalents of the appended claims.

The invention claimed is:

1. A method of performing registration between a patient space and an image space, comprising:
    imaging the patient space to generate image data of the image space, the image data comprising an image of a registration frame that is located in the patient space, the registration frame comprising a plurality of apertures;
    identifying a plurality of registration frame aperture locations within the image data, each of the plurality of aperture locations within the image data respectively corresponding to one of the plurality of apertures of the registration frame;
    identifying a pose of the registration frame within the patient space using a tracking system for the patient space;
    determining a pose of the registration frame within the image space using the plurality of registration frame aperture locations within the image data; and
    computing a transform between the patient space and the image space based on the pose of the registration frame within the patient space and the pose of the registration frame within the image space;
    wherein the image of the registration frame comprises high intensity voxels corresponding to the material of the registration frame and low intensity voxels corresponding to each of the plurality of apertures of the registration frame, and wherein identifying the plurality of registration frame aperture locations within the image data using the image of the registration frame comprises:
        performing a closing operation on the image of the registration frame to generate a closed image of the registration frame having high intensity voxels corresponding to the material of the registration frame and high intensity voxels corresponding to each of the plurality of apertures of the registration frame;
        subtracting the image of the registration frame from the closed image of the registration frame to generate an inverted image of the registration frame comprising low intensity voxels corresponding to the material of the registration frame and high intensity voxels corresponding to each of the plurality of apertures of the registration frame; and
        identifying centroids of groupings of the high intensity voxels in the inverted image of the registration frame that correspond to an expected aperture dimension as the plurality of registration frame aperture locations.

2. The method of claim 1, further comprising gray scaling the image of the registration frame based on a threshold prior to performing the closing operation.

3. The method of claim 1, wherein determining a pose of the registration frame comprises calculating an error between aperture representations of the model of the registration frame and the plurality of registration frame aperture locations within the image data.

4. The method of claim 1, wherein an aperture of the plurality of apertures is cylindrical.

5. The method of claim 1, wherein the determining a pose of the registration frame within the image space using the plurality of registration frame aperture locations within the image data comprises matching aperture representations of a model of the registration frame to the plurality of registration frame aperture locations within the image data.

6. A method of performing, registration between a patient space and an image space, comprising:
    imaging the patient space to generate image data of the image space, the image data comprising an image of a registration frame that is located in the patient space, the registration frame comprising a plurality of apertures;
    identifying a plurality of registration frame aperture locations within the image data, each of the plurality of aperture locations within the image data respectively corresponding to one of the plurality of a res of the registration frame;
    identifying a pose of the registration frame within the patient space using a tracking system for the patient space;
    determining a pose of the registration frame within the image space using the plurality of registration frame aperture locations within the image data;
    computing a transform between the patient space and the image space based on the pose of the registration frame within the patient space and the pose of the registration frame within the image space; and
    optimizing the transform by checking the symmetry of a representation of an aperture of the plurality of the apertures of the registration frame according to an adjustment of the transform.

7. The method of claim 6, wherein the pose of the registration frame within the patient space comprises a position of the registration frame within the patient space and an orientation of the registration frame within the patient space.

8. The method of claim 6, wherein imaging the patient space comprises taking a computed tomography (CT) scan of the patient space.

9. A method of performing registration between a patient space and an image space, comprising:
    imaging the patient space to generate data of the image space, the image data comprising an image of a registration frame that is located in the patient space, the registration frame comprising a plurality of apertures;

identifying a plurality of registration frame aperture locations within the image data, each of the plurality of aperture locations within the image data respectively corresponding to one of the plurality of apertures of the registration frame;
identifying a pose of the registration frame within the patient space using a tracking system for the patient space;
determining a pose of the registration frame within the image space using the plurality of registration frame aperture locations within the image data;
computing a transform between the patient space and the image space based on the pose of the registration frame within the patient space and the pose of the registration frame within the image space; and
optimizing the transform by checking an alignment between a pair of plates of material of the registration frame taken according to an adjustment of the transform.

10. The method of claim 9, wherein identifying a pose of a registration frame within the patient space using a tracking system for the patient space comprises tracking a tracking device of the registration frame with the tracking system.

11. The method of claim 7, wherein the tracking device is an infrared (IR) reflector.

12. A method of performing registration between a patient space and an image space, comprising:
imaging the patient space to generate image data of the image space, the image data comprising an image of a registration frame that is located in the patient space, the registration frame comprising a plurality of apertures;
identifying a plurality of registration frame aperture locations within the image data, each of the plurality of aperture locations within the image data respectively corresponding to one of the plurality of apertures of the registration frame;
identifying a pose of the registration frame within the patient space using a tracking system for the patient space;
determining a pose of the registration frame within the image space using the plurality of registration frame aperture locations within the image data;
computing a transform between the patient space and the image space based on se of the registration frame within the patient space and the pose of the registration frame within the image space;
generating a cropped image of the registration frame by applying the transform to the image data;
generating an optimized parameter set using a plurality of initial parameter sets and the cropped image of the registration frame; and
generating an optimized transform by applying the optimized parameter set to the transform.

13. The method of claim 12, wherein generating the optimized parameter set using the plurality of initial parameter sets with the cropped image of the registration frame comprises:
determining a sub-plurality of the plurality of initial parameter sets that has the lowest associated cost using the cropped image of the registration frame;
optimizing between the sub-plurality of the plurality of initial parameter sets to generate the optimized parameter set.

14. The method of claim 13, wherein determining the sub-plurality of the plurality of initial parameter sets that has the lowest associated cost using the cropped image of the registration frame is performed by, for each parameter set in the plurality of initial parameter sets:
creating an adjusted transform by adjusting the transform using the initial parameter set; and
comparing a first plate taken from the cropped image of the registration frame according to the adjusted transform to a second plate taken from the cropped image of the registration frame according to the adjusted transform to generate an associated cost for the initial parameter set.

15. The method of claim 13, wherein determining the sub-plurality of the plurality of initial parameter sets that has the lowest associated cost using the cropped image of the registration frame is performed by, for each initial parameter set in the plurality of initial parameter sets:
creating an updated transform by adjusting the transform using the initial parameter set;
determining a modeled aperture location within the cropped image of the registration frame by applying one of the aperture representations within the model to the cropped image of the registration frame using the updated transform; and
comparing intensity values from voxels of a first portion of the modeled aperture location to intensity values from voxels of a second portion of the modeled aperture location to generate an associated cost for the initial parameter set.

16. The method of claim 13, wherein optimizing between the sub-plurality of the plurality of parameter sets is performed using a Nelder-Mead optimization method.

17. The method of claim 12, wherein at least one of the plurality of parameter sets is determined by:
generating a secondary transform by using one fewer of the plurality of registration frame aperture locations within the image data; and
calculating a measurement between the secondary transform and the transform.

18. A computing apparatus comprising:
a processor; and
a memory storing instructions that, when executed by the processor, configure the apparatus to:
identify a pose of a registration frame within a patient space using a tracking system for the patient space, the registration frame comprising a plurality of apertures;
receive image data corresponding to an image space, the image data comprising an image of the registration frame;
identify a plurality of registration frame aperture locations within the image data, each of the plurality of aperture locations within the image data respectively corresponding to one of the plurality of apertures of the registration frame;
determine a pose of the registration frame within the image space using the plurality of registration frame aperture locations within the image data;
compute a transform between the patient space and the image space based on the pose of the registration frame within the patient space and the pose of the registration frame within the image space; and
optimize transform by checking the symmetry of a representation of an aperture of the plurality of the apertures of the registration frame according to an adjustment of the transform.

19. A non-transitory computer-readable storage medium, the computer-readable storage medium including instructions that when executed by a computer, cause the computer to:
- identify a pose of a registration frame within a patient space using a tracking system for the patient space, the registration frame comprising a plurality of apertures;
- receive image data corresponding to an image space, the image data comprising an image of the registration frame;
- identify a plurality of registration frame aperture locations within the image data using the image of the registration frame, each of the plurality of aperture locations within the image data respectively corresponding to one of the plurality of apertures of the registration frame;
- determine a pose of the registration frame within the image space using the plurality of registration frame aperture locations within the image data;
- compute a transform between the patient space and the image space based on the pose of the registration frame within the patient space and the pose of the registration frame within the image space;
- generating a cropped image of the registration frame by applying the transform to the image data;
- generating an optimize parameter set using a plurality of initial parameter sets and the cropped image of the registration frame; and
- generating an optimized transform by applying the optimized parameter set to the transform.

* * * * *